(12) United States Patent
Scheller et al.

(10) Patent No.: US 9,931,246 B2
(45) Date of Patent: *Apr. 3, 2018

(54) STEERABLE LASER PROBE

(71) Applicant: Katalyst Surgical, LLC, Chesterfield, MO (US)

(72) Inventors: Gregg D Scheller, Wildwood, MO (US); Matthew N Zeid, Ballwin, MO (US)

(73) Assignee: Katalyst Surgical, LLC, Chesterfield, MO (US)

( * ) Notice: Subject to any disclaimer, the term of this patent is extended or adjusted under 35 U.S.C. 154(b) by 940 days.

This patent is subject to a terminal disclaimer.

(21) Appl. No.: 14/027,997

(22) Filed: Sep. 16, 2013

(65) Prior Publication Data
US 2014/0107629 A1    Apr. 17, 2014

Related U.S. Application Data

(60) Provisional application No. 61/715,082, filed on Oct. 17, 2012.

(51) Int. Cl.
*A61F 9/008* (2006.01)
*A61B 18/22* (2006.01)
*A61B 18/20* (2006.01)

(52) U.S. Cl.
CPC ............ *A61F 9/008* (2013.01); *A61B 18/201* (2013.01); *A61B 18/22* (2013.01); *A61F 9/00821* (2013.01); *A61F 2009/00863* (2013.01)

(58) Field of Classification Search
CPC ............ A61F 9/008; A61F 2009/00863; A61F 9/00821; A61F 9/007; A61F 9/00802;
(Continued)

(56) References Cited

U.S. PATENT DOCUMENTS 5,190,050 A    3/1993    Nitzsche
5,355,871 A    10/1994   Hurley et al.
(Continued)

FOREIGN PATENT DOCUMENTS

EP    0900547 B1    3/1999
WO   WO 2006/091597 A1    8/2006

OTHER PUBLICATIONS

H. Fischer, B. Vogel, W. Pfleging, H. Besser, Flexible distal tip made of nitinol (NiTi) for a steerable endoscopic camera system, Materials Science and Engineering A273-275 (1999) 780-783.

*Primary Examiner* — Lynsey Eiseman
*Assistant Examiner* — Nathan A Baldwin
(74) *Attorney, Agent, or Firm* — Kevin P. Rollins

(57) ABSTRACT

A steerable laser probe may include a handle, an actuation structure having an actuation structure distal end and an actuation structure proximal end, a flexible housing tube, and an optic fiber disposed within an inner bore of the handle and the flexible housing tube. An extension of the actuation structure distal end relative to the actuation structure proximal end may be configured to gradually curve the flexible housing tube and the optic fiber. A retraction of the actuation structure distal end relative to the actuation structure proximal end may be configured to gradually straighten the flexible housing tube and the optic fiber.

20 Claims, 26 Drawing Sheets

(58) Field of Classification Search
CPC .......... A61M 25/0147; A61M 25/0136; A61M 25/0138; A61M 25/0144; A61M 25/0133; A61M 25/0141; A61M 2025/015; A61B 18/22; A61B 17/30; A61B 17/3205; A61B 17/36; A61B 17/50; A61B 1/00071; A61B 18/24; A61B 2018/225; A61B 2018/2238; A61B 2018/2288; A61B 2017/003; A61B 2017/2905; A61B 2017/2918; A61B 34/71; A61B 1/0052; A61B 1/0057
USPC .......... 600/113; 604/280; 606/1, 113, 13, 15, 606/211, 4
See application file for complete search history.

(56) References Cited

U.S. PATENT DOCUMENTS

| | | | |
|---|---|---|---|
| 5,381,782 A | 1/1995 | DeLaRama et al. | |
| 5,439,000 A | 8/1995 | Gunderson et al. | |
| 5,454,794 A | 10/1995 | Narciso et al. | |
| 5,520,222 A | 5/1996 | Chikama | |
| 6,123,699 A | 9/2000 | Webster, Jr. | |
| 6,126,654 A | 10/2000 | Giba et al. | |
| 6,198,974 B1 | 3/2001 | Webster, Jr. | |
| 6,488,695 B1* | 12/2002 | Hickingbotham | A61B 17/2909 606/206 |
| 6,505,530 B2 | 1/2003 | Adler et al. | |
| 6,530,913 B1 | 3/2003 | Giba et al. | |
| 6,551,302 B1 | 4/2003 | Rosinko et al. | |
| 6,572,608 B1* | 6/2003 | Lee | A61F 9/008 606/13 |
| 6,620,153 B2 | 9/2003 | Mueller et al. | |
| 6,730,076 B2 | 5/2004 | Hickingbotham | |
| 6,863,668 B2 | 3/2005 | Gillespie et al. | |
| 6,984,230 B2* | 1/2006 | Scheller | A61B 18/22 606/15 |
| 7,004,957 B1 | 2/2006 | Dampney et al. | |
| 7,303,533 B2 | 12/2007 | Johansen et al. | |
| 7,402,158 B2 | 7/2008 | Scheller et al. | |
| 7,632,242 B2 | 12/2009 | Griffin et al. | |
| 7,766,904 B2 | 10/2010 | McGowan, Sr. et al. | |
| 8,038,692 B2 | 10/2011 | Valencia et al. | |
| 8,075,553 B2 | 12/2011 | Scheller et al. | |
| 8,197,468 B2 | 6/2012 | Scheller et al. | |
| 9,149,389 B2* | 10/2015 | Scheller | A61B 17/30 |
| 2003/0171762 A1 | 9/2003 | Forchette et al. | |
| 2004/0181138 A1 | 9/2004 | Hindricks et al. | |
| 2004/0249367 A1 | 12/2004 | Saadat et al. | |
| 2005/0054900 A1 | 3/2005 | Mawn et al. | |
| 2005/0157985 A1 | 7/2005 | McGowan, Sr. et al. | |
| 2005/0272975 A1* | 12/2005 | McWeeney | A61B 1/00071 600/113 |
| 2007/0185514 A1 | 8/2007 | Kirchhevel | |
| 2008/0287938 A1* | 11/2008 | Scheller | A61B 18/22 606/15 |
| 2009/0018993 A1 | 1/2009 | Dick et al. | |
| 2009/0187170 A1 | 7/2009 | Auld et al. | |
| 2009/0312750 A1* | 12/2009 | Spaide | A61F 9/008 606/4 |
| 2010/0004642 A1* | 1/2010 | Lumpkin | A61B 18/22 606/4 |
| 2010/0268234 A1 | 10/2010 | Aho et al. | |
| 2011/0028947 A1 | 2/2011 | Scheller et al. | |
| 2012/0116361 A1* | 5/2012 | Hanlon | A61B 17/3205 606/1 |
| 2013/0035551 A1 | 2/2013 | Yu et al. | |
| 2013/0060240 A1 | 3/2013 | Scheller et al. | |
| 2013/0071507 A1 | 3/2013 | Scheller et al. | |
| 2013/0096541 A1 | 4/2013 | Scheller et al. | |
| 2013/0116671 A1 | 5/2013 | Scheller et al. | |
| 2013/0150838 A1 | 6/2013 | Scheller et al. | |
| 2013/0165910 A1 | 6/2013 | Scheller et al. | |

\* cited by examiner

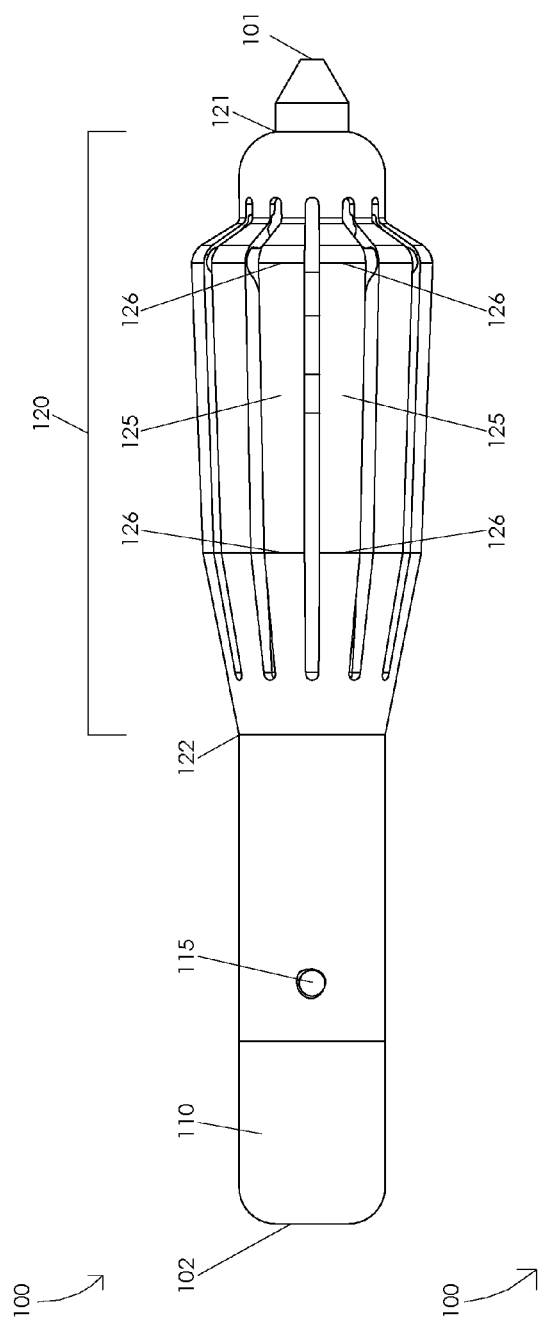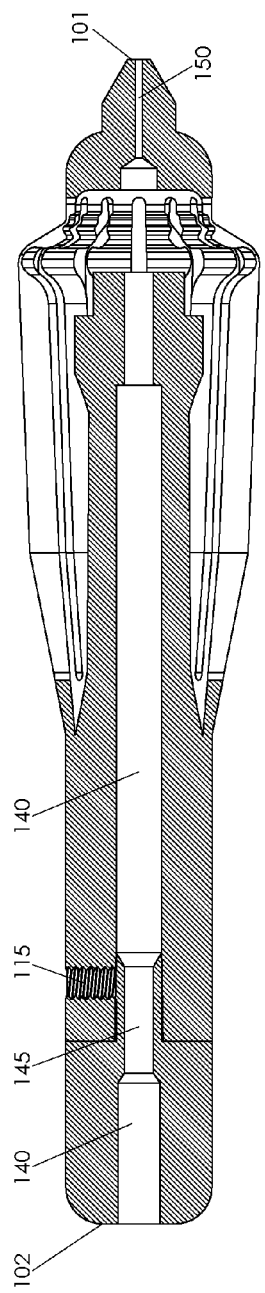
FIG. 1A
FIG. 1B

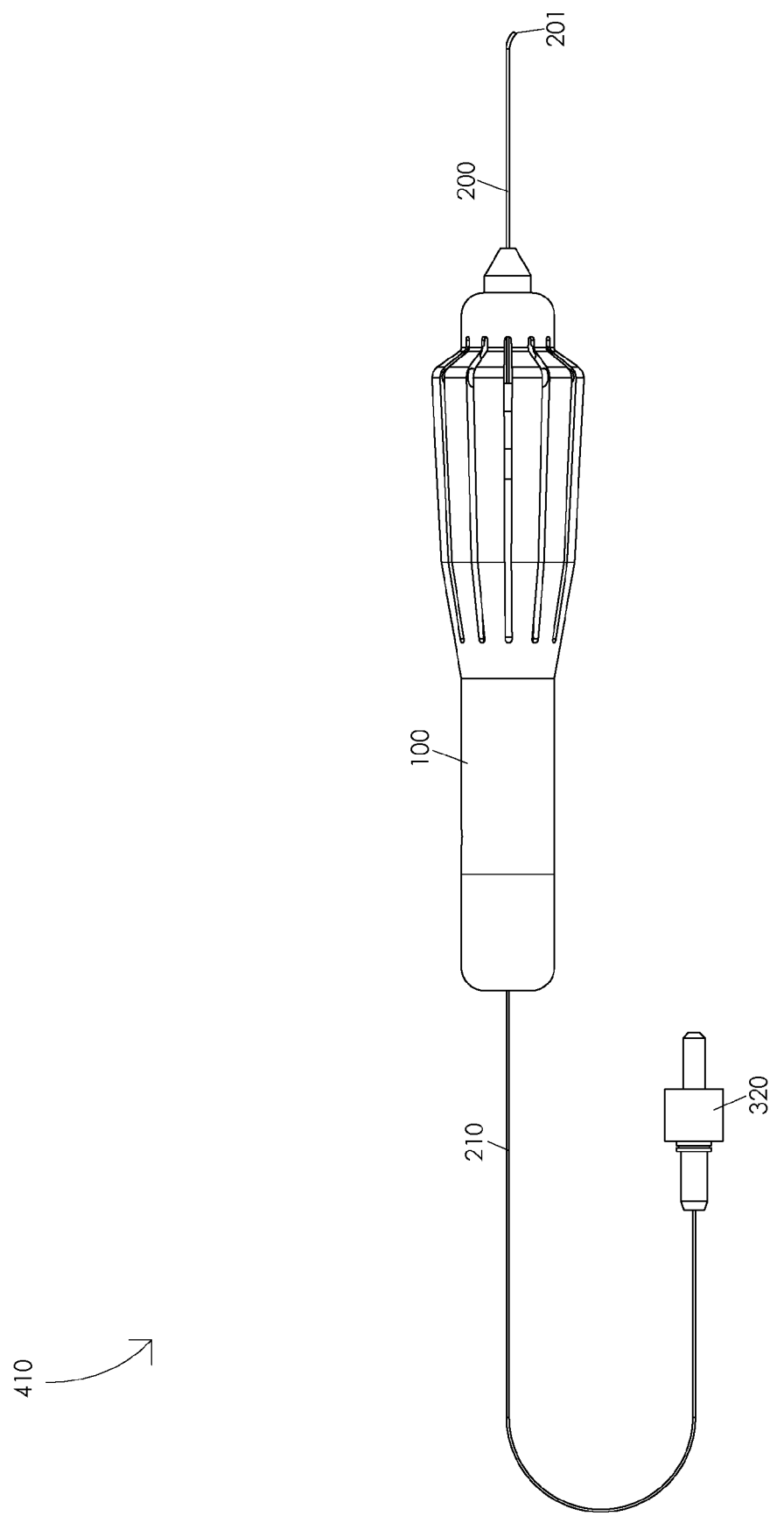

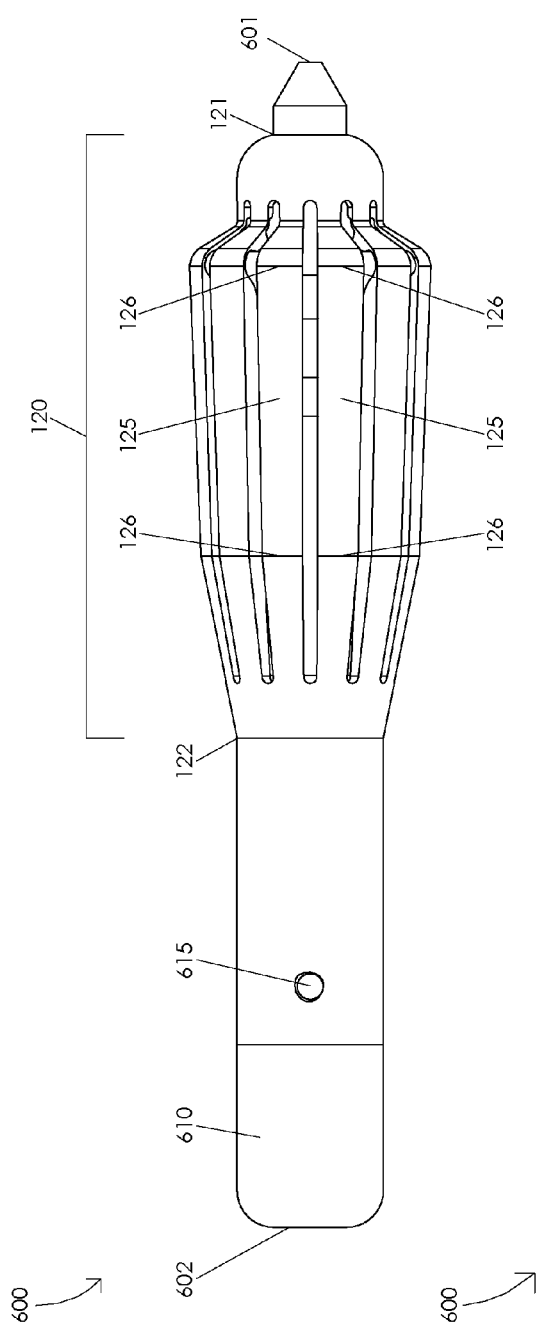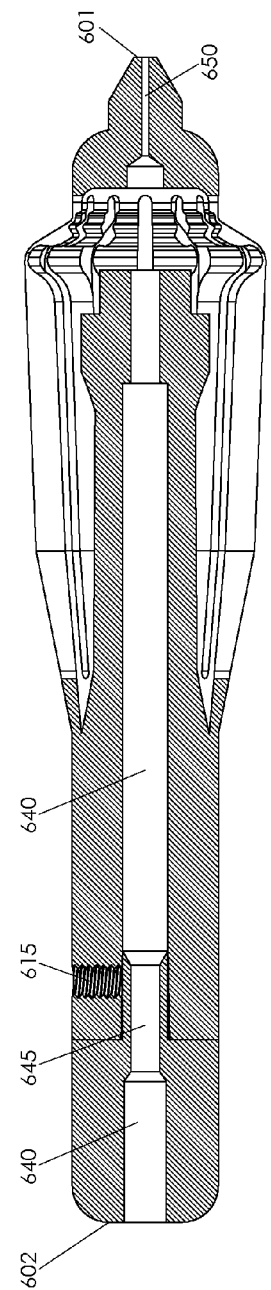

STEERABLE LASER PROBE

CROSS-REFERENCE TO RELATED APPLICATIONS

This Application claims the benefit of U.S. Provisional Application No. 61/715,082, filed Oct. 17, 2012.

FIELD OF THE INVENTION

The present disclosure relates to a surgical instrument, and, more particularly, to a steerable laser probe.

BACKGROUND OF THE INVENTION

A wide variety of ophthalmic procedures require a laser energy source. For example, ophthalmic surgeons may use laser photocoagulation to treat proliferative retinopathy. Proliferative retinopathy is a condition characterized by the development of abnormal blood vessels in the retina that grow into the vitreous humor. Ophthalmic surgeons may treat this condition by energizing a laser to cauterize portions of the retina to prevent the abnormal blood vessels from growing and hemorrhaging.

In order to increase the chances of a successful laser photocoagulation procedure, it is important that a surgeon is able aim the laser at a plurality of targets within the eye, e.g., by guiding or moving the laser from a first target to a second target within the eye. It is also important that the surgeon is able to easily control a movement of the laser. For example, the surgeon must be able to easily direct a laser beam by steering the beam to a first position aimed at a first target, guide the laser beam from the first position to a second position aimed at a second target, and hold the laser beam in the second position. Accordingly, there is a need for a surgical laser probe that can be easily guided to a plurality of targets within the eye.

BRIEF SUMMARY OF THE INVENTION

The present disclosure presents a steerable laser probe. In one or more embodiments, a steerable laser probe may comprise a handle, an actuation structure having an actuation structure distal end and an actuation structure proximal end, a flexible housing tube, and an optic fiber disposed within an inner bore of the handle and the flexible housing tube. Illustratively, a compression of the actuation structure may be configured to extend the actuation structure distal end relative to the actuation structure proximal end. In one or more embodiments, an extension of the actuation structure distal end relative to the actuation structure proximal end may be configured to gradually curve the flexible housing tube and the optic fiber. Illustratively, a decompression of the actuation structure may be configured to retract the actuation structure distal end relative to the actuation structure proximal end. In one or more embodiments, a retraction of the actuation structure distal end relative to the actuation structure proximal end may be configured to gradually straighten the flexible housing tube and the optic fiber.

BRIEF DESCRIPTION OF THE DRAWINGS

The above and further advantages of the present invention may be better understood by referring to the following description in conjunction with the accompanying drawings in which like reference numerals indicate identical or functionally similar elements:

FIGS. 1A and 1B are schematic diagrams illustrating a handle;

FIGS. 4A, 4B, 4C, 4D, and 4E are schematic diagrams illustrating a gradual curving of an optic fiber;

FIGS. 6A and 6B are schematic diagrams illustrating a handle;

DETAILED DESCRIPTION OF AN ILLUSTRATIVE EMBODIMENT

Figure 2:
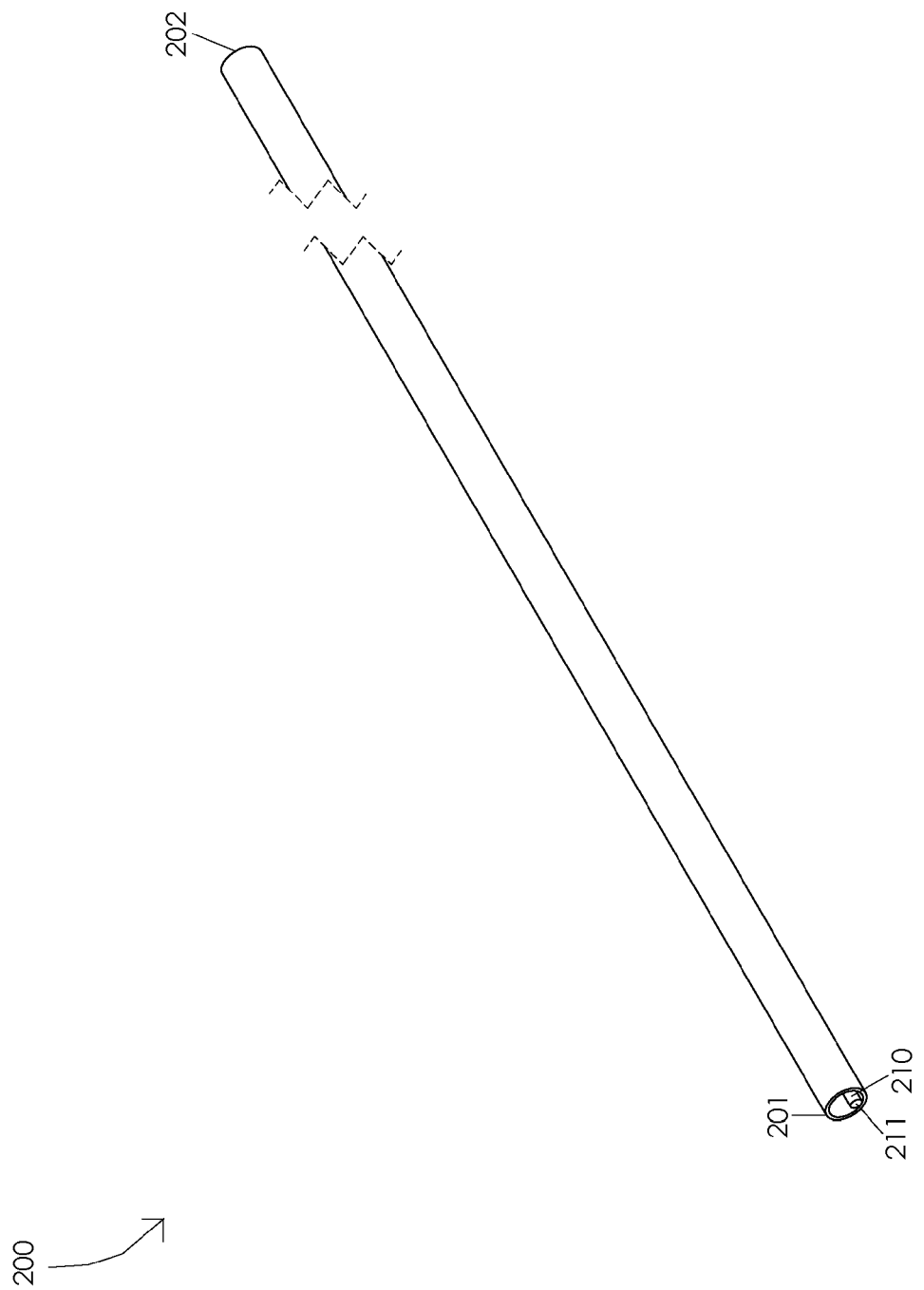
FIG. 2 is a schematic diagram illustrating a flexible housing tube.

FIGS. 1A and 1B are schematic diagrams illustrating a handle 100. FIG. 1A illustrates a top view of a handle 100. Illustratively, handle 100 may comprise a handle distal end 101, a handle proximal end 102, a handle end plug 110, a fixation mechanism housing 115, and an actuation structure 120 having an actuation structure distal end 121 and an actuation structure proximal end 122. In one or more embodiments, actuation structure 120 may comprise a plurality of actuation arms 125. Illustratively, each actuation arm 125 of a plurality of actuation arms 125 may comprise one or more extension joints 126. In one or more embodiments, an application of a force to actuation structure 120 may be configured to compress actuation structure 120. For example, a surgeon may compress actuation structure 120 by applying a force to a portion of actuation structure 120. Illustratively, an application of a force to a portion of an actuation arm 125 of a plurality of actuation arms 125 may be configured to compress actuation structure 120. For example, a surgeon may compress actuation structure 120 by applying a force to a portion of an actuation arm 125 of a plurality of actuation arms 125.

In one or more embodiments, actuation structure 120 may be compressed by an application of one or more forces at one or more locations around an outer perimeter of actuation structure 120. Illustratively, the one or more locations may comprise any of a plurality of locations around the outer perimeter of actuation structure 120. For example, a surgeon may compress actuation structure 120 by squeezing actuation structure 120. Illustratively, the surgeon may compress actuation structure 120 by squeezing actuation structure 120 at any particular location of a plurality of locations around an outer perimeter of actuation structure 120. For example, a surgeon may rotate handle 100 and compress actuation structure 120 in any rotational orientation of a plurality of rotational orientations of handle 100.

In one or more embodiments, a compression of actuation structure 120 may be configured to increase a distance between actuation structure distal end 121 and actuation structure proximal end 122. Illustratively, a compression of actuation structure 120 may be configured to extend actuation structure distal end 121 relative to actuation structure proximal end 122. In one or more embodiments, an application of a force having a magnitude in a range of 0.6 to 1.6 pounds to a portion of actuation structure 120 may be configured to compress actuation structure 120, e.g., an application of a force having a magnitude of 1.1 pounds to a portion of actuation structure 120 may be configured to compress actuation structure 120. Illustratively, an application of a force having a magnitude less than 0.6 pounds or greater than 1.6 pounds to a portion of actuation structure 120 may be configured to compress actuation structure 120. In one or more embodiments, a compression of actuation structure 120 may be configured to extend actuation structure distal end 121 in a range of 0.02 to 0.06 inches relative to actuation structure proximal end 122. Illustratively, a compression of actuation structure 120 may be configured to extend actuation structure distal end 121 less than 0.02 inches or greater than 0.06 inches relative to actuation structure proximal end 122. In one or more embodiments, a compression of actuation structure 120 may be configured to increase a distance between actuation structure distal end 121 and actuation structure proximal end 122 in a range of 0.5 to 2.5 percent. Illustratively, a compression of actuation structure 120 may be configured to increase a distance between actuation structure distal end 121 and actuation structure proximal end 122 by less than 0.5 percent or greater than 2.5 percent. In one or more embodiments, a compression of actuation structure 120 may be configured to increase a distance between handle distal end 101 and handle proximal end 102. Illustratively, a compression of actuation structure 120 may be configured to extend handle distal end 101 relative to handle proximal end 102. In one or more embodiments, a compression of actuation structure 120 may be configured to expand an extension joint 126 of a particular actuation arm 125 of a plurality of actuation arms 125. Illustratively, an expansion of an extension joint 126 of a particular actuation arm 125 may be configured to extend the particular actuation arm 125, e.g., by increasing a distance between a distal end of the particular actuation arm 125 and a proximal end of the particular actuation arm 125. In one or more embodiments, an expansion of an extension joint 126 of a particular actuation arm 125 may be configured to extend a distal end of the particular arm 125 relative to actuation structure proximal end 122. Illustratively, an expansion of an extension joint 126 of a particular actuation arm 125 may be configured to expand an extension joint 126 of each actuation arm 125 of a plurality of actuation arms 125. In one or more embodiments, an expansion of an extension joint 126 of a particular actuation arm 125 may be configured to extend actuation structure distal end 121 relative to actuation structure proximal end 122. Illustratively, an expansion of an extension joint 126 of a particular actuation arm 125 may be configured to extend handle distal end 101 relative to handle proximal end 102. In one or more embodiments, a compression of actuation structure 120 may be configured to expand a plurality of extension joints 126 of a particular actuation arm 125. Illustratively, an expansion of a plurality of extension joints 126 of a particular actuation arm 125 may be configured to expand a plurality of extension joints 126 of each actuation arm 125 of a plurality of actuation arms. In one or more embodiments, an expansion of a plurality of extension joints 126 of a particular actuation arm 125 may be configured to extend actuation structure distal end 121 relative to actuation structure proximal end 122. Illustratively, an expansion of a plurality of extension joints 126 of a particular actuation arm 125 may be configured to extend handle distal end 101 relative to handle proximal end 102.

In one or more embodiments, a decompression of actuation structure 120 may be configured to decrease a distance between actuation structure distal end 121 and actuation structure proximal end 122. Illustratively, a decompression of actuation structure 120 may be configured to retract actuation structure distal end 121 relative to actuation structure proximal end 122. In one or more embodiments, a removal of a force having a magnitude in a range of 0.6 to 1.6 pounds from a portion of actuation structure 120 may be configured to decompress actuation structure 120, e.g., a removal of a force having a magnitude of 1.1 pounds from a portion of actuation structure 120 may be configured to decompress actuation structure 120. Illustratively, a removal of a force having a magnitude less than 0.6 pounds or greater than 1.6 pounds from a portion of actuation structure 120 may be configured to decompress actuation structure 120. In one or more embodiments, a decompression of actuation structure 120 may be configured to retract actuation structure distal end 121 in a range of 0.02 to 0.06 inches relative to actuation structure proximal end 122. Illustratively, a decompression of actuation structure 120 may be configured to retract actuation structure distal end 121 less than 0.02 inches or greater than 0.06 inches relative to actuation structure proximal end 122. In one or more embodiments, a decompression of actuation structure 120 may be configured to decrease a distance between actuation structure distal end 121 and actuation structure proximal end 122 in a range of 0.5 to 2.5 percent. Illustratively, a decompression of actuation structure 120 may be configured to decrease a distance between actuation structure distal end 121 and actuation structure proximal end 122 by less than 0.5 percent or greater than 2.5 percent. In one or more embodiments, a decompression of actuation structure 120 may be configured to decrease a distance between handle distal end 101 and handle proximal end 102. Illustratively, a decompression of actuation structure 120 may be configured to retract handle distal end 101 relative to handle proximal end 102. In one or more embodiments, a decompression of actuation structure 120 may be configured to collapse an extension joint 126 of a particular actuation arm 125 of a plurality of actuation arms 125. Illustratively, a collapse of an extension joint 126 of a particular actuation arm 125 may be configured to retract the particular actuation arm 125, e.g., by decreasing a distance between a distal end of the particular actuation arm 125 and a proximal end of the particular actuation arm 125. In one or more embodiments, a collapse of an extension joint 126 of a particular actuation arm 125 may be configured to retract a distal end of the particular arm 125 relative to actuation structure proximal end 122. Illustratively, a collapse of an extension joint 126 of a particular actuation arm 125 may be configured to collapse an extension joint 126 of each actuation arm 125 of a plurality of actuation arms 125. In one or more embodiments, a collapse of an extension joint 126 of a particular actuation arm 125 may be configured to retract actuation structure distal end 121 relative to actuation structure proximal end 122. Illustratively, a collapse of an extension joint 126 of a particular actuation arm 125 may be configured to retract handle distal end 101 relative to handle proximal end 102. In one or more embodiments, a decompression of actuation structure 120 may be configured to collapse a plurality of extension joints 126 of a particular actuation arm 125. Illustratively, a collapse of a plurality of extension joints 126 of a particular actuation arm 125 may be configured to collapse a plurality of extension joints 126 of each actuation arm 125 of a plurality of actuation arms. In one or more embodiments, a collapse of a plurality of extension joints 126 of a particular actuation arm 125 may be configured to retract actuation structure distal end 121 relative to actuation structure proximal end 122. Illustratively, a collapse of a plurality of extension joints 126 of a particular actuation arm 125 may be configured to retract handle distal end 101 relative to handle proximal end 102.

In one or more embodiments, actuation structure 120 may be manufactured from any suitable material, e.g., polymers, metals, metal alloys, etc., or from any combination of suitable materials. Illustratively, actuation structure 120 may be manufactured from a shape memory material. In one or more embodiments, actuation structure 120 may be manufactured using a selective laser sintering machine. Illustratively, actuation structure 100 may be manufactured by additive manufacturing or 3D printing. In one or more embodiments, actuation structure 120 may be manufactured from a material suitable for sterilization by a medical autoclave. Illustratively, actuation structure 120 may be manufactured from a material, e.g., Nylon, configured to withstand exposure to temperatures, pressures, and ambient conditions present in a medical autoclave without degradation. For example, actuation structure 120 may be configured to function normally after exposure in a temperature 250° F. for 15 minutes at an atmospheric pressure of 15 psi. In one or more embodiments, actuation structure 120 may be configured to be used in a surgical procedure and then sterilized by a medical autoclave at least three times. Illustratively, actuation structure 120 may be configured to be used in a surgical procedure and then sterilized by a medical autoclave more than three times.

In one or more embodiments, actuation structure 120 may have a density in a range of 0.02 to 0.06 pounds per cubic inch, e.g., actuation structure 120 may have a density of 0.041 pounds per cubic inch. Illustratively, actuation structure 120 may have a density less than 0.02 pounds per cubic inch or greater than 0.06 pounds per cubic inch. In one or more embodiments, actuation structure 120 may have a mass in a range of 0.01 to 0.03 pounds, e.g., actuation structure 120 may have a mass of 0.024 pounds. Illustratively, actuation structure 120 may have a mass less than 0.01 pounds or greater than 0.03 pounds. In one or more embodiments, actuation structure 120 may have a volume in a range of 0.3 to 0.7 cubic inches, e.g., actuation structure 120 may have a volume of 0.577 cubic inches. Illustratively, actuation structure 120 may have a volume less than 0.3 cubic inches or greater than 0.7 cubic inches. In one or more embodiments, actuation structure 120 may have a surface area in a range of 10.0 to 20.0 square inches, e.g., actuation structure 120 may have a surface area of 14.87 square inches. Illustratively, actuation structure 120 may have a surface area less than 10.0 square inches or greater than 20.0 square inches.

FIG. 1B illustrates a cross-sectional view of a handle 100. Illustratively, handle 100 may comprise an inner bore 140, an optic fiber housing 145, and a flexible housing tube housing 150. In one or more embodiments, handle 100 may be manufactured from any suitable material, e.g., polymers, metals, metal alloys, etc., or from any combination of suitable materials.

FIG. 2 is a schematic diagram illustrating a flexible housing tube 200. Illustratively, flexible housing tube 200 may comprise a flexible housing tube distal end 201 and a flexible housing tube proximal end 202. Flexible housing tube 200 may be manufactured from any suitable material, e.g., polymers, metals, metal alloys, etc., or from any combination of suitable materials. Illustratively, flexible housing tube 200 may comprise a shape memory material, e.g., Nitinol. In one or more embodiments, flexible housing tube 200 may be manufactured from a material having a ultimate tensile strength in a range of 700 to 1000 MPa. Illustratively, flexible housing tube 200 may be manufactured from a material having ultimate tensile strength less than 700 MPa or greater than 1000 MPa. In one or more embodiments, flexible housing tube 200 may be manufactured from a material having a modulus of elasticity in a range of 30 to 80 GPa. Illustratively, flexible housing tube 200 may be manufactured from a material having a modulus of elasticity less than 30 GPa or greater than 80 GPa.

In one or more embodiments, flexible housing tube 200 may be manufactured with dimensions suitable for performing microsurgical procedures, e.g., ophthalmic surgical procedures. Illustratively, flexible housing tube 200 may be manufactured at gauge sizes commonly used in ophthalmic surgical procedures, e.g., 23 gauge, 25 gauge, etc. In one or more embodiments, flexible housing tube 200 may be configured to be inserted in a cannula, e.g., a cannula used during an ophthalmic surgical procedure. For example, one or more properties of flexible housing tube 200 may be optimized to reduce friction as flexible housing tube 200 is inserted into a cannula. In one or more embodiments, one or more properties of flexible housing tube 200 may be optimized to reduce friction as flexible housing tube 200 is removed from a cannula. Illustratively, flexible housing tube 200 may have an ultimate tensile strength in a range of 1000 to 1100 MPa. In one or more embodiments, flexible housing tube 200 may have an ultimate tensile strength less than 1000 MPa or greater than 1100 MPa.

In one or more embodiments, an optic fiber 210 may be disposed within flexible housing tube 200. Illustratively, optic fiber 210 may comprise an optic fiber distal end 211 and an optic fiber proximal end 212. In one or more embodiments, optic fiber 210 may be configured to transmit light, e.g., laser light. Illustratively, optic fiber 210 may be disposed within flexible housing tube 200 wherein optic fiber distal end 211 may be adjacent to flexible housing tube distal end 201. In one or more embodiments, a portion of optic fiber 210 may be fixed to a portion of flexible housing tube 200, e.g., by an adhesive or any suitable fixation means.

Figure 3:
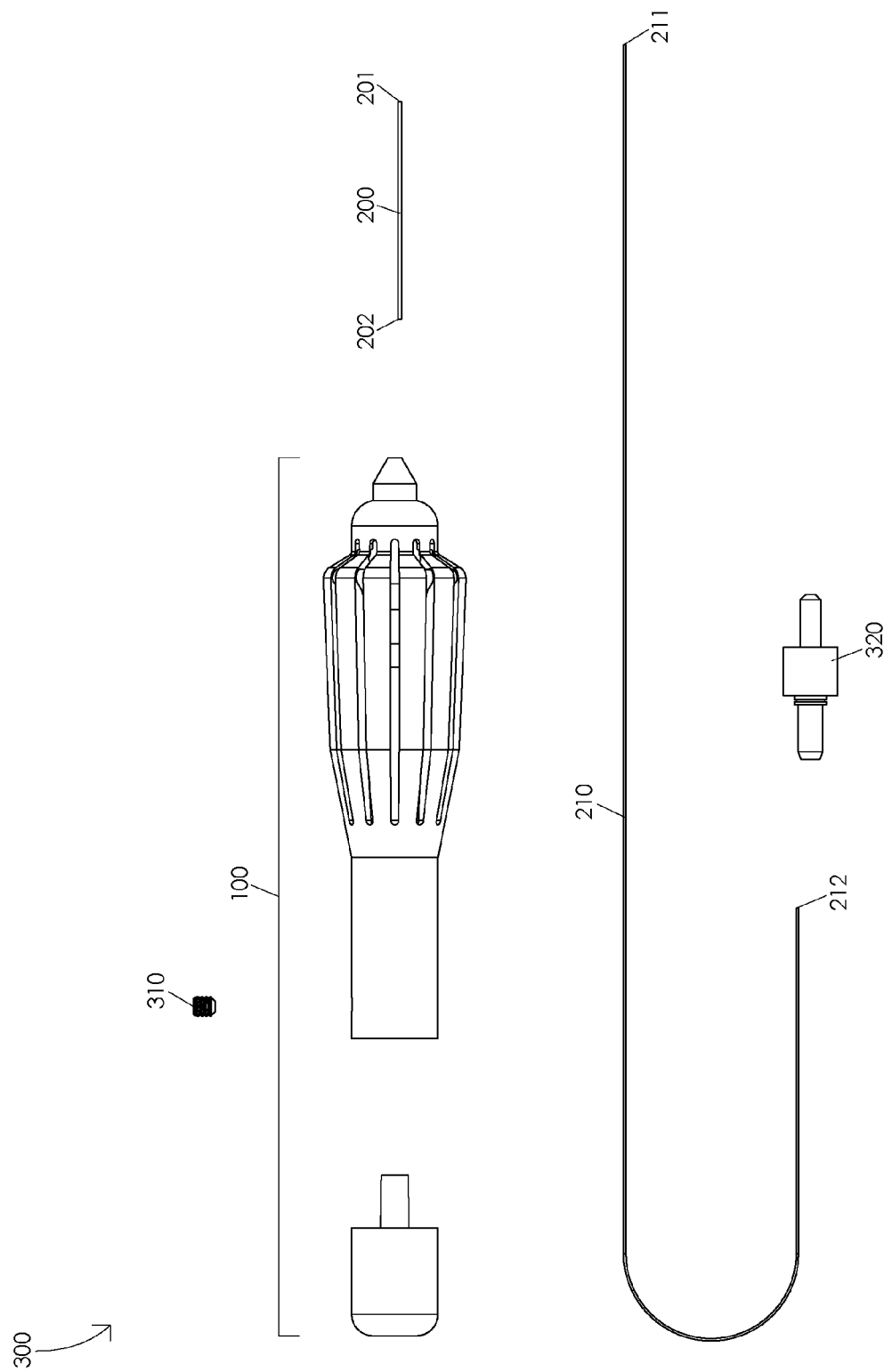
FIG. 3 is a schematic diagram illustrating an exploded view of a steerable laser probe assembly.

FIG. 3 is a schematic diagram illustrating an exploded view of a steerable laser probe assembly 300. In one or more embodiments, a steerable laser probe assembly 300 may comprise a handle 100, a flexible housing tube 200 having a flexible housing tube distal end 201 and a flexible housing tube proximal end 202, an optic fiber 210 having an optic fiber distal end 211 and an optic fiber proximal end 212, a fixation mechanism 310, and a light source interface 320. Illustratively, light source interface 320 may be configured to interface with optic fiber 210, e.g., at optic fiber proximal end 212. In one or more embodiments, light source interface 320 may comprise a standard light source connecter, e.g., an SMA connector.

Illustratively, a portion of flexible housing tube 200 may be fixed to a portion of handle 100, e.g., flexible housing tube proximal end 202 may be fixed to handle distal end 101. In one or more embodiments, a portion of flexible housing tube 200 may be fixed to a portion of handle 100, e.g., by an adhesive or any suitable fixation means. Illustratively, a portion of flexible housing tube 200 may be disposed within flexible housing tube housing 150, e.g., flexible housing tube proximal end 202 may be disposed within flexible housing tube housing 150. In one or more embodiments, a portion of flexible housing tube 200 may be fixed within flexible housing tube housing 150, e.g., by an adhesive or any suitable fixation means. For example, flexible housing tube 200 may be fixed within flexible housing tube housing 150 by a press fit, a weld, a setscrew, etc.

Illustratively, optic fiber 210 may be disposed within inner bore 140, optic fiber housing 145, flexible housing tube housing 150, and flexible housing tube 200. In one or more embodiments, optic fiber 210 may be disposed within flexible housing tube 200 wherein optic fiber distal end 211 may be adjacent to flexible housing tube distal end 201. In one or more embodiments, a portion of optic fiber 210 may be fixed to a portion of flexible housing tube 200, e.g., by an adhesive or any suitable fixation means. Illustratively, a portion of optic fiber 210 may be fixed within optic fiber housing 145, e.g., by an adhesive or any suitable fixation means. In one or more embodiments, fixation mechanism 310 may be configured to fix a portion of optic fiber 210 within optic fiber housing 145, e.g., fixation mechanism 310 may be disposed within fixation mechanism housing 115 and optic fiber housing 145. Illustratively, fixation mechanism 310 may be configured to fix a portion of optic fiber 210 within optic fiber housing 145, e.g., by a press fit or any suitable fixation means. In one or more embodiments, fixation mechanism 310 may comprise a set screw, e.g., configured to fix a portion of optic fiber 210 within optic fiber housing 145.

Illustratively, a compression of actuation structure 120 may be configured to extend actuation structure distal end 121 relative to actuation structure proximal end 122. In one or more embodiments, an extension of actuation structure distal end 121 relative to actuation structure proximal end 122 may be configured to extend handle distal end 101 relative to handle proximal end 102. Illustratively, an extension of handle distal end 101 relative to handle proximal end 102 may be configured to extend flexible housing tube 200 relative to handle proximal end 102. In one or more embodiments, an extension of flexible housing tube 200 relative to handle proximal end 102 may be configured to extend flexible housing tube 200 relative to optic fiber 210. Illustratively, a portion of optic fiber 210, e.g., a portion of optic fiber 210 fixed to flexible housing tube 200, may be configured to resist an extension of flexible housing tube 200 relative to optic fiber 210. In one or more embodiments, an extension of flexible housing tube 200 relative to optic fiber 210 may be configured to compress a portion of flexible housing tube 200, e.g., a portion of optic fiber 210 fixed to a portion of flexible housing tube 200 may be configured compress a portion of flexible housing tube 200. Illustratively, a compression of a portion of flexible housing tube 200 may be configured to cause flexible housing tube 200 to gradually curve. In one or more embodiments, a gradual curving of flexible housing tube 200 may be configured to gradually curve optic fiber 210. Illustratively, a compression of actuation structure 120 may be configured to gradually curve flexible housing tube 200. In one or more embodiments, a compression of actuation structure 120 may be configured to gradually curve optic fiber 210.

Illustratively, a decompression of actuation structure 120 may be configured to retract actuation structure distal end 121 relative to actuation structure proximal end 122. In one or more embodiments, a retraction of actuation structure distal end 121 relative to actuation structure proximal end 122 may be configured to retract handle distal end 101 relative to handle proximal end 102. Illustratively, a retraction of handle distal end 101 relative to handle proximal end 102 may be configured to retract flexible housing tube 200 relative to handle proximal end 102. In one or more embodiments, a retraction of flexible housing tube 200 relative to handle proximal end 102 may be configured to retract flexible housing tube 200 relative to optic fiber 210. Illustratively, a portion of optic fiber 210, e.g., a portion of optic fiber 210 fixed to flexible housing tube 200, may be configured to facilitate a retraction of flexible housing tube 200 relative to optic fiber 210. In one or more embodiments, a retraction of flexible housing tube 200 relative to optic fiber 210 may be configured to decompress a portion of flexible housing tube 200, e.g., a portion of optic fiber 210 fixed to a portion of flexible housing tube 200 may be configured decompress a portion of flexible housing tube 200. Illustratively, a decompression of a portion of flexible housing tube 200 may be configured to cause flexible housing tube 200 to gradually straighten. In one or more embodiments, a gradual straightening of flexible housing tube 200 may be configured to gradually straighten optic fiber 210. Illustratively, a decompression of actuation structure 120 may be configured to gradually straighten flexible housing tube 200. In one or more embodiments, a decompression of actuation structure 120 may be configured to gradually straighten optic fiber 210.

Figure 4A:
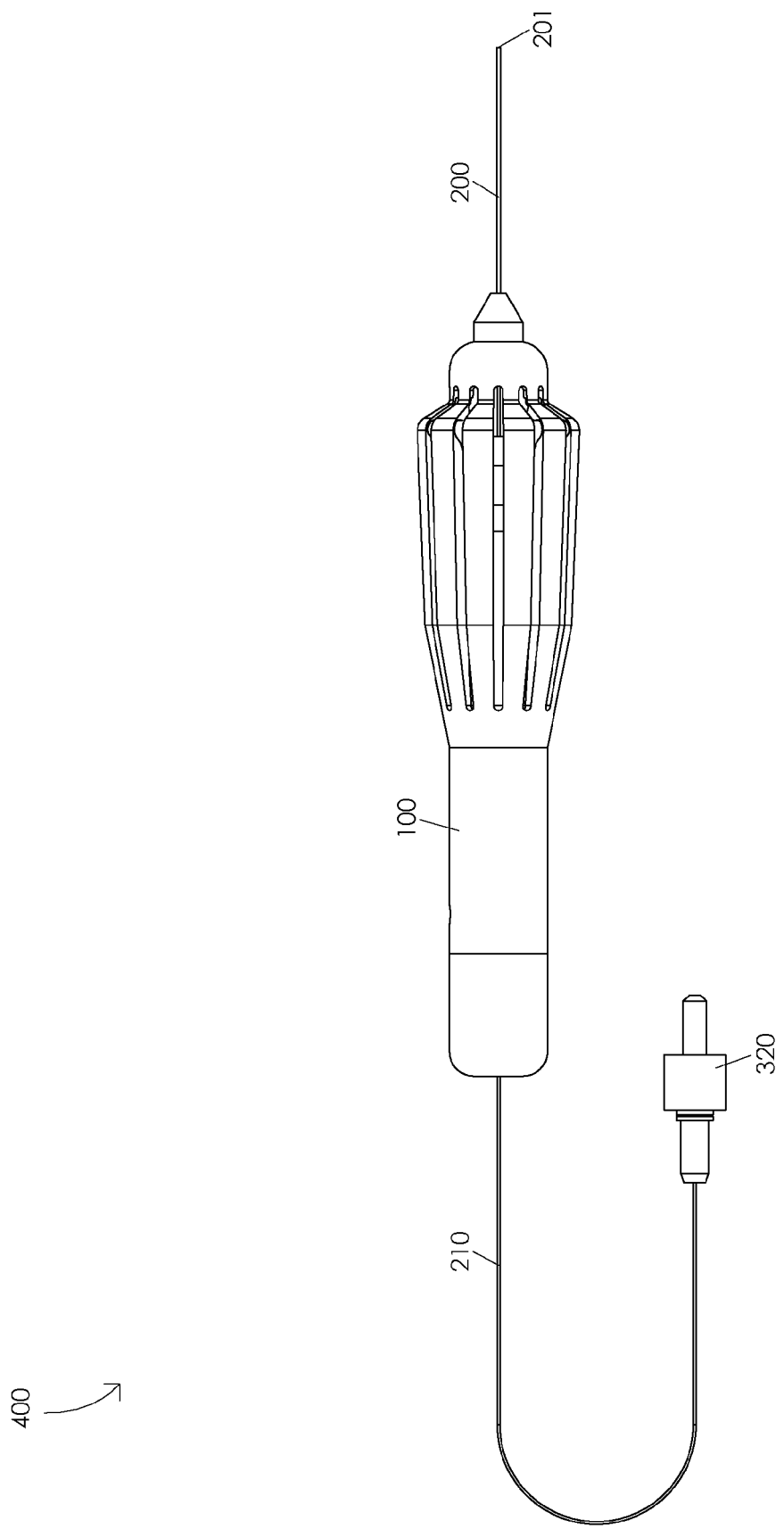

FIGS. 4A, 4B, 4C, 4D, and 4E are schematic diagrams illustrating a gradual curving of an optic fiber 210. FIG. 4A illustrates a straight optic fiber 400. In one or more embodiments, optic fiber 210 may comprise a straight optic fiber 400, e.g., when actuation structure 120 is fully decompressed. Illustratively, optic fiber 210 may comprise a straight optic fiber 400, e.g., when flexible housing tube 200 is fully retracted relative to optic fiber 210. Illustratively, a line tangent to optic fiber distal end 211 may be parallel to a line tangent to flexible housing tube proximal end 202, e.g., when optic fiber 210 comprises a straight optic fiber 400.

FIG. 4B illustrates an optic fiber in a first curved position 410. In one or more embodiments, a compression of actuation structure 120 may be configured to gradually curve optic fiber 210 from a straight optic fiber 400 to an optic fiber in a first curved position 410. Illustratively, a compression of actuation structure 120 may be configured to extend actuation structure distal end 121 relative to actuation structure proximal end 122. In one or more embodiments, an extension of actuation structure distal 121 end relative to actuation structure proximal end 122 may be configured to extend flexible housing tube 200 relative to optic fiber 210. Illustratively, an extension of flexible housing tube 200 relative to optic fiber 210 may be configured to compress a portion of flexible housing tube 200. In one or more embodiments, a compression of a portion of flexible housing tube 200 may be configured to gradually curve flexible housing tube 200. Illustratively, a gradual curving of flexible housing tube 200 may be configured to gradually curve optic fiber 210, e.g., from a straight optic fiber 400 to an optic fiber in a first curved position 410. In one or more embodiments, a line tangent to optic fiber distal end 211 may intersect a line tangent to flexible housing tube proximal end 202 at a first angle, e.g., when optic fiber 210 comprises an optic fiber in a first curved position 410. In one or more embodiments, the first angle may comprise any angle greater than zero degrees. For example, the first angle may comprise a 45 degree angle.

Figure 4C:
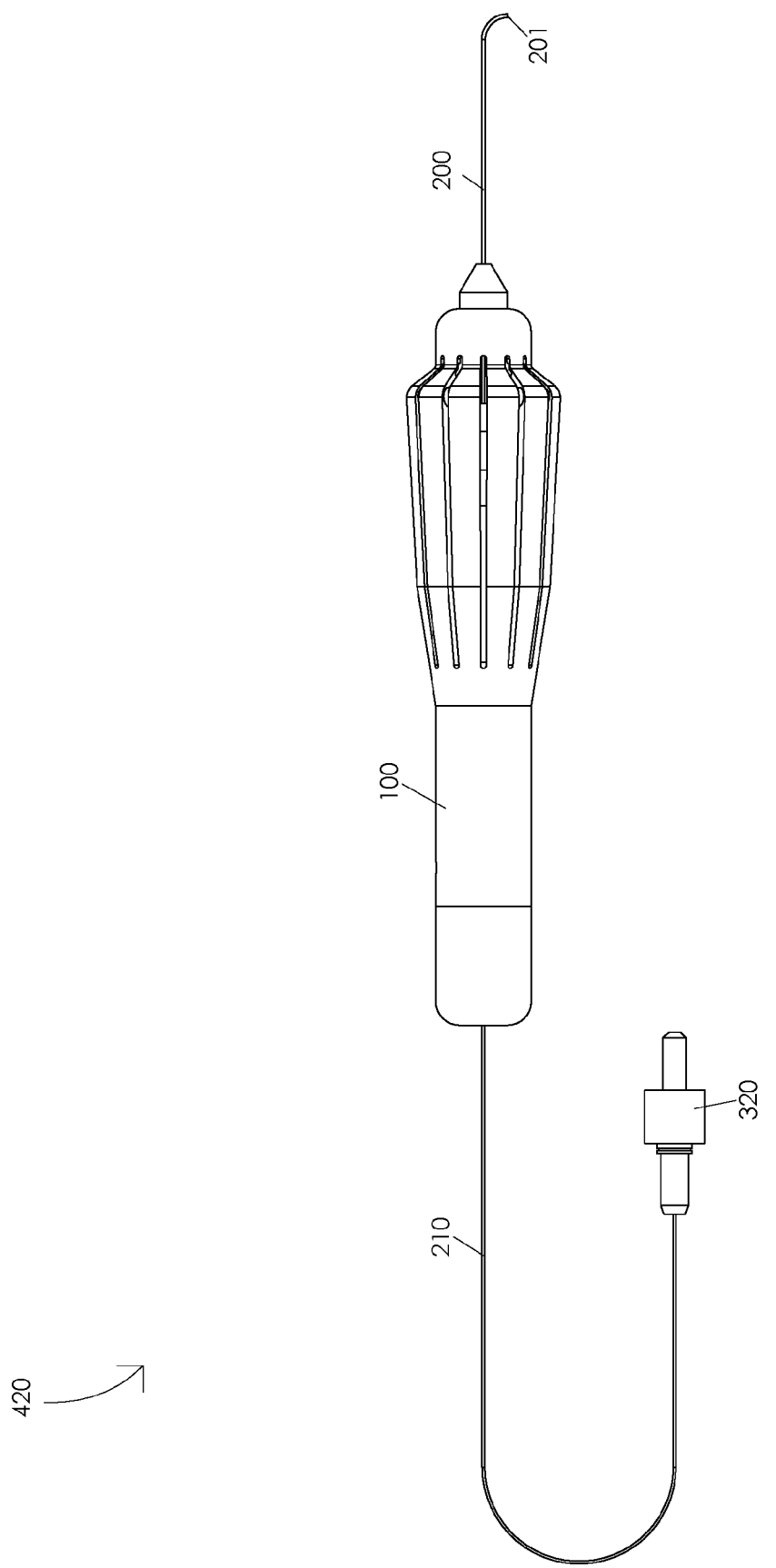

FIG. 4C illustrates an optic fiber in a second curved position 420. In one or more embodiments, a compression of actuation structure 120 may be configured to gradually curve optic fiber 210 from an optic fiber in a first curved position 410 to an optic fiber in a second curved position 420. Illustratively, a compression of actuation structure 120 may be configured to extend actuation structure distal end 121 relative to actuation structure proximal end 122. In one or more embodiments, an extension of actuation structure distal 121 end relative to actuation structure proximal end 122 may be configured to extend flexible housing tube 200 relative to optic fiber 210. Illustratively, an extension of flexible housing tube 200 relative to optic fiber 210 may be configured to compress a portion of flexible housing tube 200. In one or more embodiments, a compression of a portion of flexible housing tube 200 may be configured to gradually curve flexible housing tube 200. Illustratively, a gradual curving of flexible housing tube 200 may be configured to gradually curve optic fiber 210, e.g., from an optic fiber in a first curved position 410 to an optic fiber in a second curved position 420. In one or more embodiments, a line tangent to optic fiber distal end 211 may intersect a line tangent to flexible housing tube proximal end 202 at a second angle, e.g., when optic fiber 210 comprises an optic fiber in a second curved position 420. In one or more embodiments, the second angle may comprise any angle greater than the first angle. For example, the second angle may comprise a 90 degree angle.

Figure 4D:
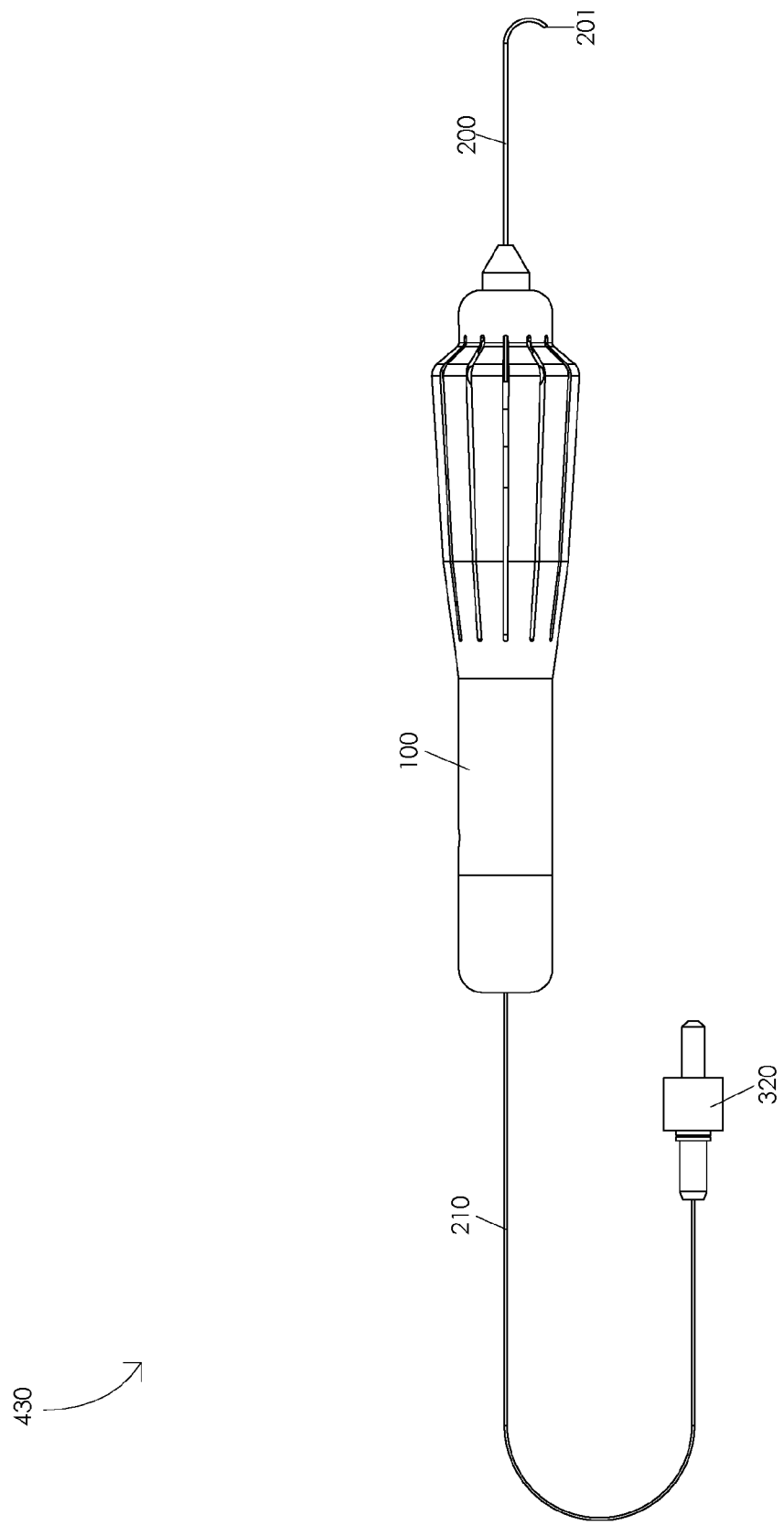

FIG. 4D illustrates an optic fiber in a third curved position 430. In one or more embodiments, a compression of actuation structure 120 may be configured to gradually curve optic fiber 210 from an optic fiber in a second curved position 420 to an optic fiber in a third curved position 430. Illustratively, a compression of actuation structure 120 may be configured to extend actuation structure distal end 121 relative to actuation structure proximal end 122. In one or more embodiments, an extension of actuation structure distal 121 end relative to actuation structure proximal end 122 may be configured to extend flexible housing tube 200 relative to optic fiber 210. Illustratively, an extension of flexible housing tube 200 relative to optic fiber 210 may be configured to compress a portion of flexible housing tube 200. In one or more embodiments, a compression of a portion of flexible housing tube 200 may be configured to gradually curve flexible housing tube 200. Illustratively, a gradual curving of flexible housing tube 200 may be configured to gradually curve optic fiber 210, e.g., from an optic fiber in a second curved position 420 to an optic fiber in a third curved position 430. In one or more embodiments, a line tangent to optic fiber distal end 211 may intersect a line tangent to flexible housing tube proximal end 202 at a third angle, e.g., when optic fiber 210 comprises an optic fiber in a third curved position 430. In one or more embodiments, the third angle may comprise any angle greater than the second angle. For example, the third angle may comprise a 135 degree angle.

Figure 4E:
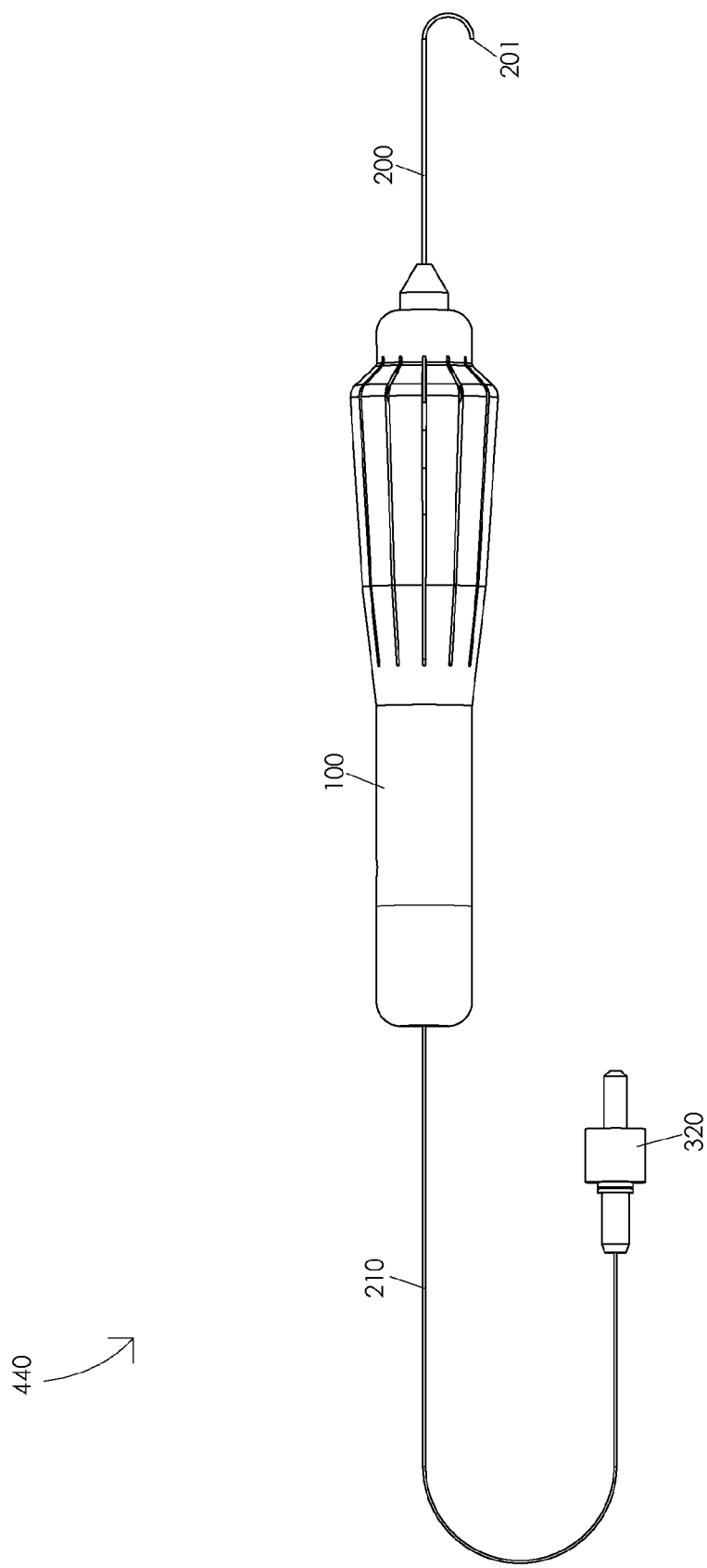

FIG. 4E illustrates an optic fiber in a fourth curved position 440. In one or more embodiments, a compression of actuation structure 120 may be configured to gradually curve optic fiber 210 from an optic fiber in a third curved position 430 to an optic fiber in a fourth curved position 440. Illustratively, a compression of actuation structure 120 may be configured to extend actuation structure distal end 121 relative to actuation structure proximal end 122. In one or more embodiments, an extension of actuation structure distal 121 end relative to actuation structure proximal end 122 may be configured to extend flexible housing tube 200 relative to optic fiber 210. Illustratively, an extension of flexible housing tube 200 relative to optic fiber 210 may be configured to compress a portion of flexible housing tube 200. In one or more embodiments, a compression of a portion of flexible housing tube 200 may be configured to gradually curve flexible housing tube 200. Illustratively, a gradual curving of flexible housing tube 200 may be configured to gradually curve optic fiber 210, e.g., from an optic fiber in a third curved position 430 to an optic fiber in a fourth curved position 440. In one or more embodiments, a line tangent to optic fiber distal end 211 may be parallel to a line tangent to flexible housing tube proximal end 202, e.g., when optic fiber 210 comprises an optic fiber in a fourth curved position 440.

In one or more embodiments, one or more properties of a steerable laser probe may be adjusted to attain one or more desired steerable laser probe features. Illustratively, a length that flexible housing tube distal end 201 extends from handle distal end 101 may be adjusted to vary an amount of compression of actuation structure 120 configured to curve flexible housing tube 200 to a particular curved position. In one or more embodiments, a stiffness of flexible housing tube 200 may be adjusted to vary an amount of compression of actuation structure 120 configured to curve flexible housing tube 200 to a particular curved position. Illustratively, a material comprising flexible housing tube 200 may be adjusted to vary an amount of compression of actuation structure 120 configured to curve flexible housing tube 200 to a particular curved position. In one or more embodiments, a geometry of actuation structure 120 may be adjusted to vary an amount of compression of actuation structure 120 configured to curve flexible housing tube 200 to a particular curved position. Illustratively, one or more locations within flexible housing tube 200 wherein optic fiber 210 may be fixed to a portion of flexible housing tube 200 may be adjusted to vary an amount of compression of actuation structure 120 configured to curve flexible housing tube 200 to a particular curved position.

In one or more embodiments, at least a portion of optic fiber 210 may be enclosed in an optic fiber sleeve configured to, e.g., protect optic fiber 210, vary a stiffness of optic fiber 210, vary an optical property of optic fiber 210, etc. Illustratively, an optic fiber sleeve may be configured to compress a portion of flexible housing tube 200. In one or more embodiments, a portion of an optic fiber sleeve may be fixed within optic fiber housing 145, e.g., by an adhesive or any suitable fixation means. Illustratively, a portion of an optic fiber sleeve may be fixed to a portion of flexible housing tube 200, e.g., by an adhesive or any suitable fixation means. In one or more embodiments, a compression of actuation structure 120 may be configured to extend flexible housing tube 200 relative to an optic fiber sleeve. Illustratively, a portion of an optic fiber sleeve, e.g., a portion of an optic fiber sleeve fixed to a portion of flexible housing tube 200, may be configured to resist an extension of flexible housing tube 200 relative to the optic fiber sleeve. In one or more embodiments, an extension of flexible housing tube 200 relative to an optic fiber sleeve may be configured to compress a portion of flexible housing tube 200. Illustratively, a compression of a portion of flexible housing tube 200 may be configured to gradually curve flexible housing tube 200. In one or more embodiments, a gradual curving of flexible housing tube 200 may be configured to gradually curve optic fiber 210.

Illustratively, optic fiber 210 may comprise a buffer, a cladding disposed in the buffer, and a core disposed in the cladding. In one or more embodiments, at least a portion of optic fiber 210 may comprise a buffer configured to protect an optical property of optic fiber 210. Illustratively, at least a portion of optic fiber 210 may comprise a buffer configured to protect an optical layer of optic fiber 210, e.g., the buffer may protect an optical layer of a curved portion of optic fiber 210. In one or more embodiments, at least a portion of optic fiber 210 may comprise a polyimide buffer configured to protect an optical property of optic fiber 210. For example, at least a portion of optic fiber 210 may comprise a Kapton buffer configured to protect an optical property of optic fiber 210.

Illustratively, a steerable laser probe may be configured to indicate, e.g., to a surgeon, a direction that optic fiber 210 may curve, e.g., due to a compression of actuation structure 120. In one or more embodiments, a portion of a steerable laser probe, e.g., handle 100, may be marked in a manner configured to indicate a direction that optic fiber 210 may curve. For example, a portion of handle 100 may comprise an arrow marking configured to indicate a direction that optic fiber 210 may curve. Illustratively, a portion of flexible housing tube 200 may comprise a mark configured to indicate a direction that optic fiber 210 may curve. In one or more embodiments, flexible housing tube 200 may comprise a slight curve, e.g., a curve less than 7.5 degrees, when actuation structure 120 is fully decompressed. Illustratively, flexible housing tube 200 may comprise a slight curve, e.g., a curve equal to or greater than 7.5 degrees, when actuation structure 120 is fully decompressed. In one or more embodiments, flexible housing tube 200 may comprise a slight curve configured to indicate a direction that optic fiber 210 may curve, e.g., due to a compression of actuation structure 120.

Figure 5A:
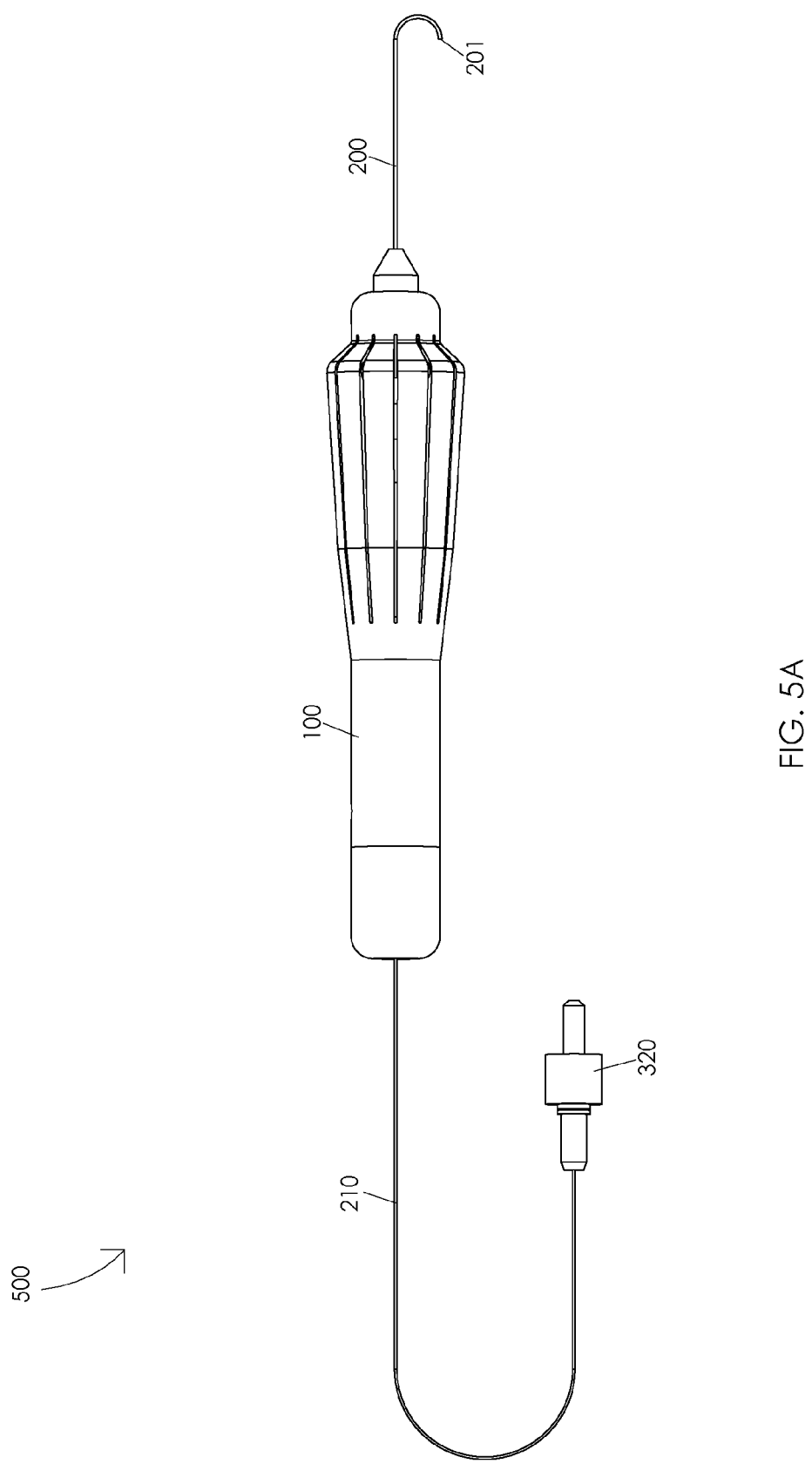
FIGS. 5A, 5B, 5C, 5D, and 5E are schematic diagrams illustrating a gradual straightening of an optic fiber.

FIGS. 5A, 5B, 5C, 5D, and 5E are schematic diagrams illustrating a gradual straightening of an optic fiber 210. FIG. 5A illustrates a fully curved optic fiber 500. In one or more embodiments, optic fiber 210 may comprise a fully curved optic fiber 500, e.g., when actuation structure 120 is fully compressed. Illustratively, optic fiber 210 may comprise a fully curved optic fiber 500, e.g., when flexible housing tube 200 is fully extended relative to optic fiber 210. In one or more embodiments, a line tangent to optic fiber distal end 211 may be parallel to a line tangent to flexible housing tube proximal end 202, e.g., when optic fiber 210 comprises a fully curved optic fiber 500.

Figure 5B:
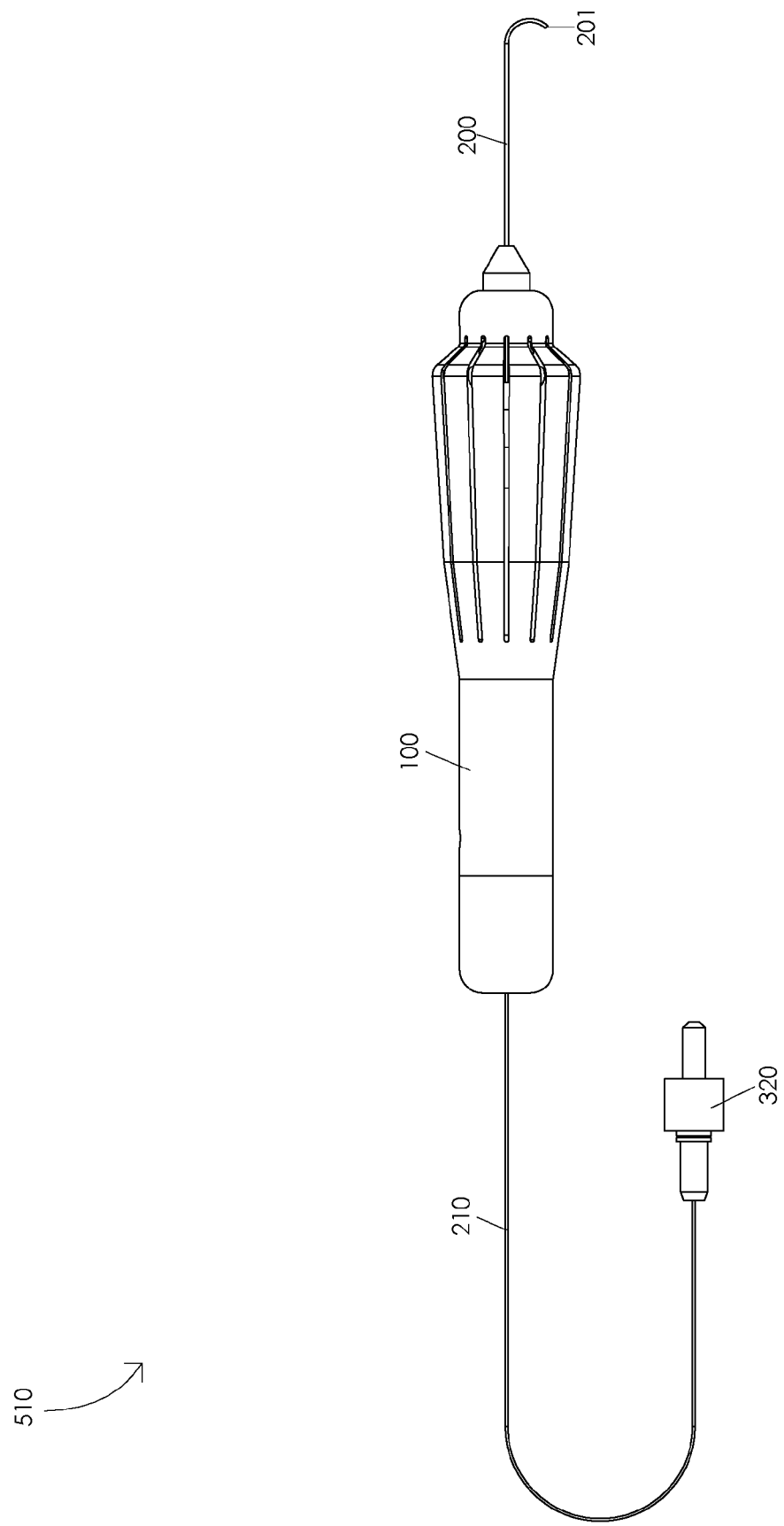

FIG. 5B illustrates an optic fiber in a first partially straightened position 510. In one or more embodiments, a decompression of actuation structure 120 may be configured to gradually straighten optic fiber 210 from a fully curved optic fiber 500 to an optic fiber in a first partially straightened position 510. Illustratively, a decompression of actuation structure 120 may be configured to retract actuation structure distal end 121 relative to actuation structure proximal end 122. In one or more embodiments, a retraction of actuation structure distal end 121 relative to actuation structure proximal end 122 may be configured to retract flexible housing tube 200 relative to optic fiber 210. Illustratively, a portion of optic fiber 210, e.g., a portion of optic fiber 210 fixed to a portion of flexible housing tube 200, may be configured to facilitate a retraction of flexible housing tube 200 relative to optic fiber 210. In one or more embodiments, a retraction of flexible housing tube 200 relative to optic fiber 210 may be configured to decompress a portion of flexible housing tube 200. Illustratively, a decompression of a portion of flexible housing tube 200 may be configured to gradually straighten flexible housing tube 200. In one or more embodiments, a gradual straightening of flexible housing tube 200 may be configured to gradually straighten optic fiber 210, e.g., from a fully curved optic fiber 500 to an optic fiber in a first partially straightened position 510. Illustratively, a line tangent to optic fiber distal end 211 may intersect a line tangent to flexible housing tube proximal end 202 at a first partially straightened angle, e.g., when optic fiber 210 comprises an optic fiber in a first partially straightened position 510. In one or more embodiments, the first partially straightened angle may comprise any angle less than 180 degrees. For example, the first partially straightened angle may comprise a 135 degree angle.

Figure 5C:
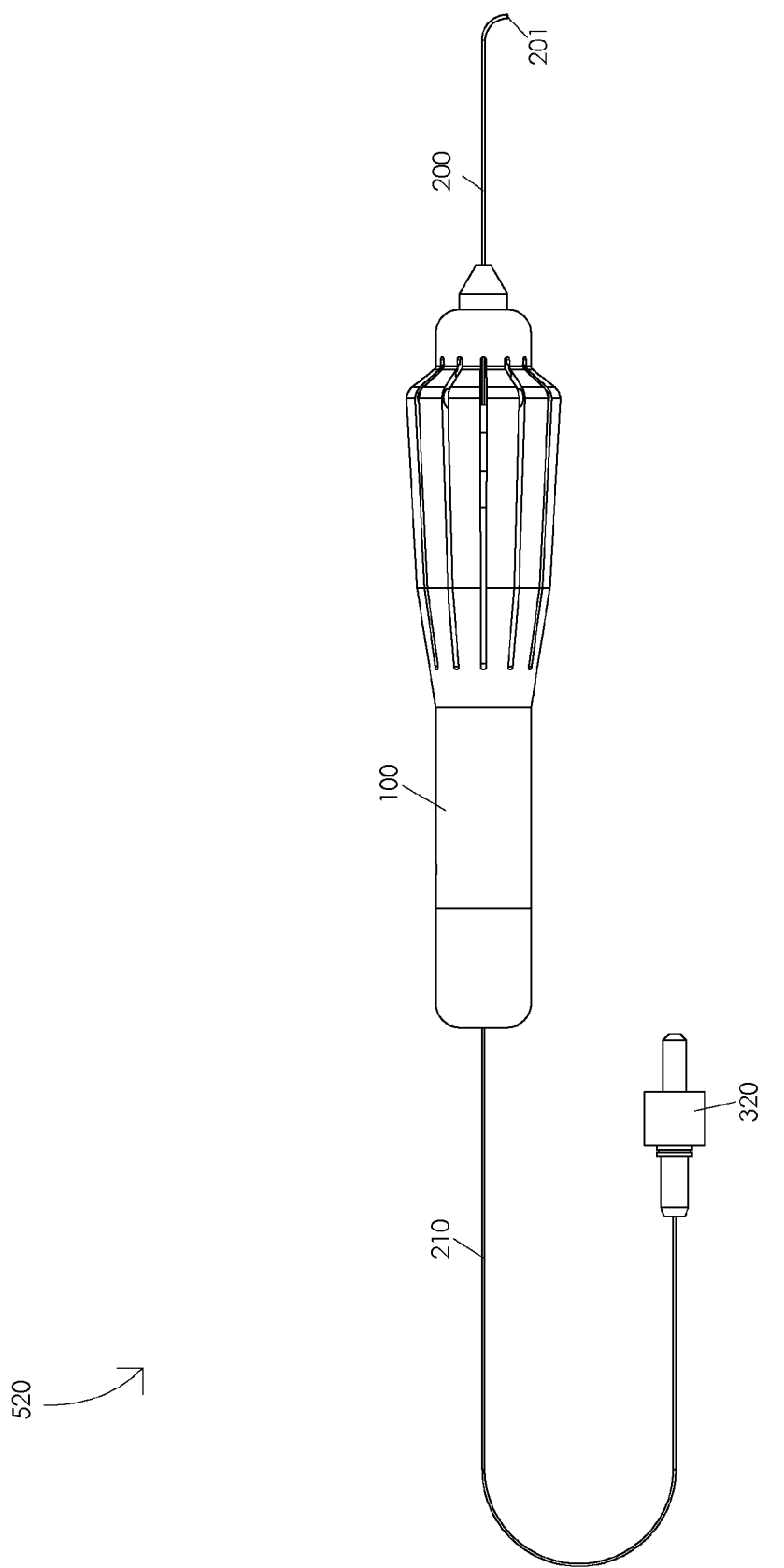

FIG. 5C illustrates an optic fiber in a second partially straightened position 520. In one or more embodiments, a decompression of actuation structure 120 may be configured to gradually straighten optic fiber 210 from an optic fiber in a first partially straightened position 510 to an optic fiber in a second partially straightened position 520. Illustratively, a decompression of actuation structure 120 may be configured to retract actuation structure distal end 121 relative to actuation structure proximal end 122. In one or more embodiments, a retraction of actuation structure distal end 121 relative to actuation structure proximal end 122 may be configured to retract flexible housing tube 200 relative to optic fiber 210. Illustratively, a portion of optic fiber 210, e.g., a portion of optic fiber 210 fixed to a portion of flexible housing tube 200, may be configured to facilitate a refraction of flexible housing tube 200 relative to optic fiber 210. In one or more embodiments, a retraction of flexible housing tube 200 relative to optic fiber 210 may be configured to decompress a portion of flexible housing tube 200. Illustratively, a decompression of a portion of flexible housing tube 200 may be configured to gradually straighten flexible housing tube 200. In one or more embodiments, a gradual straightening of flexible housing tube 200 may be configured to gradually straighten optic fiber 210, e.g., from an optic fiber in a first partially straightened position 510 to an optic fiber in a second partially straightened position 520. Illustratively, a line tangent to optic fiber distal end 211 may intersect a line tangent to flexible housing tube proximal end 202 at a second partially straightened angle, e.g., when optic fiber 210 comprises an optic fiber in a second partially straightened position 520. In one or more embodiments, the second partially straightened angle may comprise any angle less than the first partially straightened angle. For example, the second partially straightened angle may comprise a 90 degree angle.

Figure 5D:
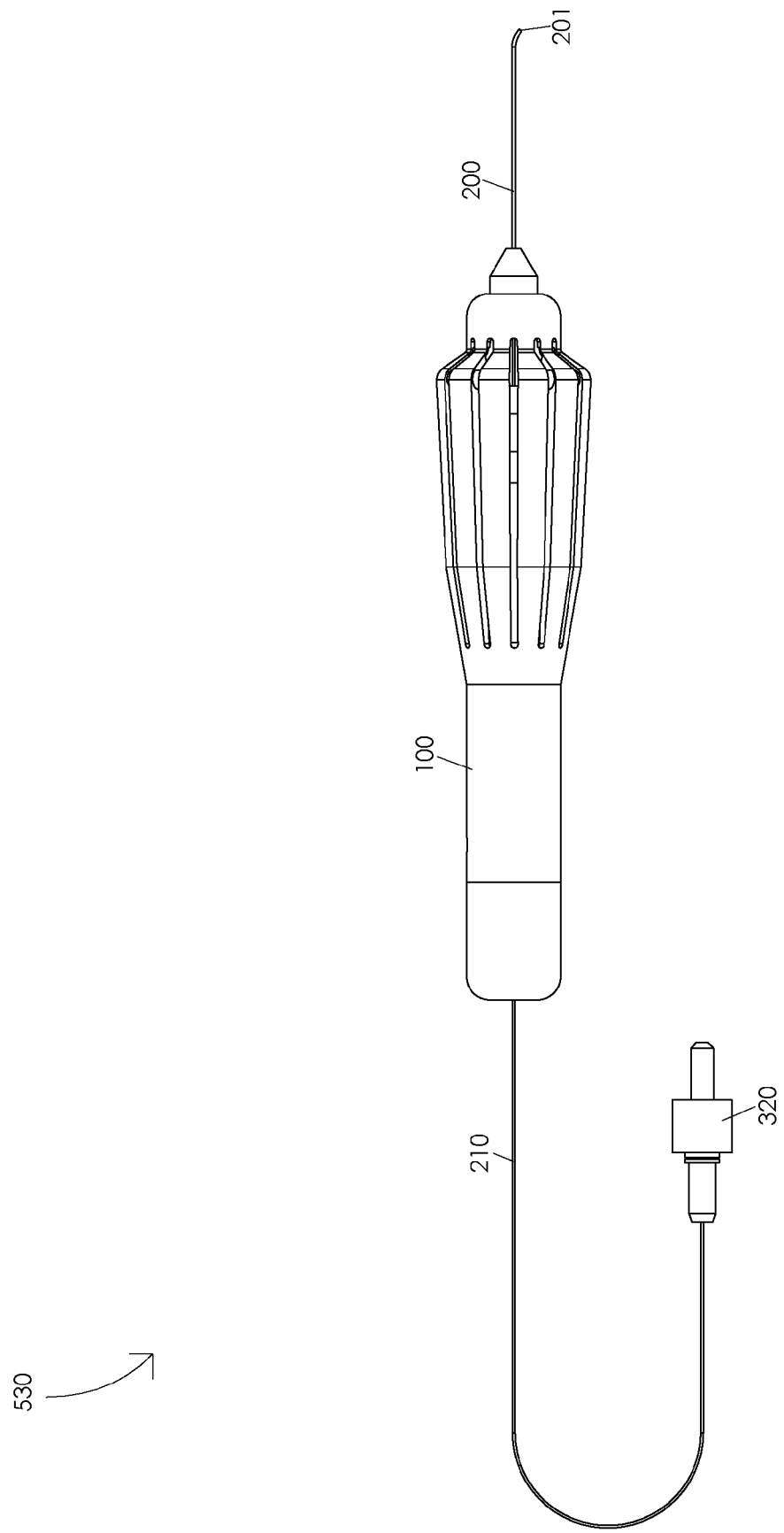

FIG. 5D illustrates an optic fiber in a third partially straightened position 530. In one or more embodiments, a decompression of actuation structure 120 may be configured to gradually straighten optic fiber 210 from an optic fiber in a second partially straightened position 520 to an optic fiber in a third partially straightened position 530. Illustratively, a decompression of actuation structure 120 may be configured to retract actuation structure distal end 121 relative to actuation structure proximal end 122. In one or more embodiments, a retraction of actuation structure distal end 121 relative to actuation structure proximal end 122 may be configured to retract flexible housing tube 200 relative to optic fiber 210. Illustratively, a portion of optic fiber 210, e.g., a portion of optic fiber 210 fixed to a portion of flexible housing tube 200, may be configured to facilitate a retraction of flexible housing tube 200 relative to optic fiber 210. In one or more embodiments, a refraction of flexible housing tube 200 relative to optic fiber 210 may be configured to decompress a portion of flexible housing tube 200. Illustratively, a decompression of a portion of flexible housing tube 200 may be configured to gradually straighten flexible housing tube 200. In one or more embodiments, a gradual straightening of flexible housing tube 200 may be configured to gradually straighten optic fiber 210, e.g., from an optic fiber in a second partially straightened position 520 to an optic fiber in a third partially straightened position 530. Illustratively, a line tangent to optic fiber distal end 211 may intersect a line tangent to flexible housing tube proximal end 202 at a third partially straightened angle, e.g., when optic fiber 210 comprises an optic fiber in a third partially straightened position 530. In one or more embodiments, the third partially straightened angle may comprise any angle less than the second partially straightened angle. For example, the third partially straightened angle may comprise a 45 degree angle.

Figure 5E:
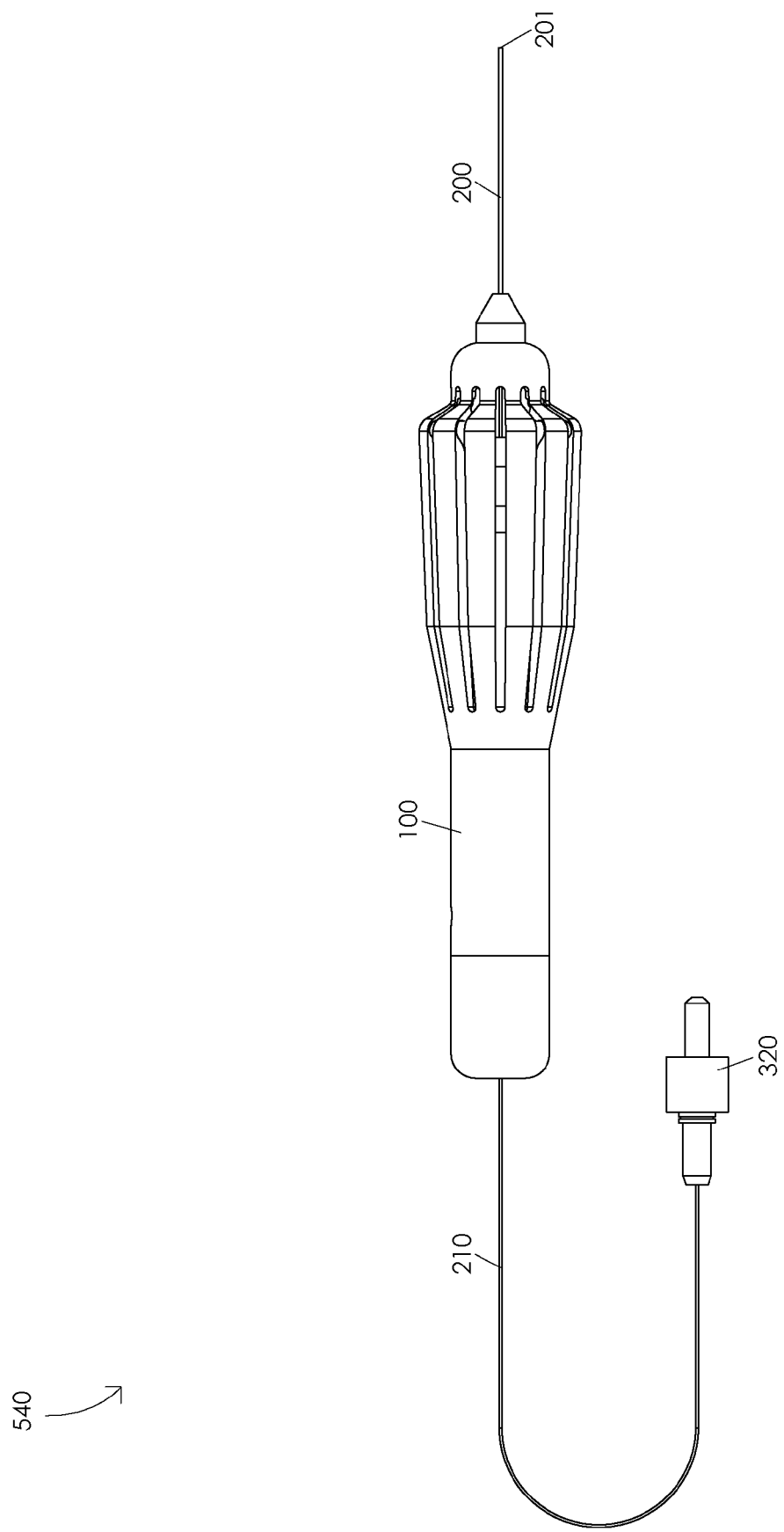

FIG. 5E illustrates an optic fiber in a fully straightened position 540. In one or more embodiments, a decompression of actuation structure 120 may be configured to gradually straighten optic fiber 210 from an optic fiber in a third partially straightened position 530 to an optic fiber in a fully straightened position 540. Illustratively, a decompression of actuation structure 120 may be configured to retract actuation structure distal end 121 relative to actuation structure proximal end 122. In one or more embodiments, a refraction of actuation structure distal end 121 relative to actuation structure proximal end 122 may be configured to retract flexible housing tube 200 relative to optic fiber 210. Illustratively, a portion of optic fiber 210, e.g., a portion of optic fiber 210 fixed to a portion of flexible housing tube 200, may be configured to facilitate a retraction of flexible housing tube 200 relative to optic fiber 210. In one or more embodiments, a refraction of flexible housing tube 200 relative to optic fiber 210 may be configured to decompress a portion of flexible housing tube 200. Illustratively, a decompression of a portion of flexible housing tube 200 may be configured to gradually straighten flexible housing tube 200. In one or more embodiments, a gradual straightening of flexible housing tube 200 may be configured to gradually straighten optic fiber 210, e.g., from an optic fiber in a third partially straightened position 530 to an optic fiber in a fully straightened position 540. Illustratively, a line tangent to optic fiber distal end 211 may be parallel to a line tangent to flexible housing tube proximal end 202, e.g., when optic fiber 210 comprises an optic fiber in a fully straightened position 540.

Illustratively, a surgeon may aim optic fiber distal end 211 at any of a plurality of targets within an eye, e.g., to perform a photocoagulation procedure, to illuminate a surgical target site, etc. In one or more embodiments, a surgeon may aim optic fiber distal end 211 at any target within a particular transverse plane of the inner eye by, e.g., rotating handle 100 to orient flexible housing tube 200 in an orientation configured to cause a curvature of flexible housing tube 200 within the particular transverse plane of the inner eye and varying an amount of compression of actuation structure 120. Illustratively, a surgeon may aim optic fiber distal end 211 at any target within a particular sagittal plane of the inner eye by, e.g., rotating handle 100 to orient flexible housing tube 200 in an orientation configured to cause a curvature of flexible housing tube 200 within the particular sagittal plane of the inner eye and varying an amount of compression of actuation structure 120. In one or more embodiments, a surgeon may aim optic fiber distal end 211 at any target within a particular frontal plane of the inner eye by, e.g., varying an amount of compression of actuation structure 120 to orient a line tangent to optic fiber distal end 211 wherein the line tangent to optic fiber distal end 211 is within the particular frontal plane of the inner eye and rotating handle 100. Illustratively, a surgeon may aim optic fiber distal end 211 at any target located outside of the particular transverse plane, the particular sagittal plane, and the particular frontal plane of the inner eye, e.g., by varying a rotational orientation of handle 100 and varying an amount of compression of actuation structure 120. In one or more embodiments, a surgeon may aim optic fiber distal end 211 at any target of a plurality of targets within an eye, e.g., without increasing a length of a portion of a steerable laser probe within the eye.

Illustratively, a surgeon may aim optic fiber distal end 211 at any target of a plurality of targets within an eye, e.g., without decreasing a length of a portion of a steerable laser probe within the eye.

FIGS. 6A and 6B are schematic diagrams illustrating a handle 600. FIG. 6A illustrates a top view of a handle 600. Illustratively, handle 600 may comprise a handle distal end 601, a handle proximal end 602, a handle end plug 610, a fixation mechanism housing 615, and an actuation structure 120 having an actuation structure distal end 121 and an actuation structure proximal end 122. In one or more embodiments, actuation structure 120 may comprise a plurality of actuation arms 125. Illustratively, each actuation arm 125 of a plurality of actuation arms 125 may comprise one or more extension joints 126. FIG. 6B illustrates a cross-sectional view of a handle 600. Illustratively, handle 600 may comprise an inner bore 640, a cable housing 645, and a flexible housing tube housing 650. In one or more embodiments, handle 600 may be manufactured from any suitable material, e.g., polymers, metals, metal alloys, etc., or from any combination of suitable materials.

Figure 7:
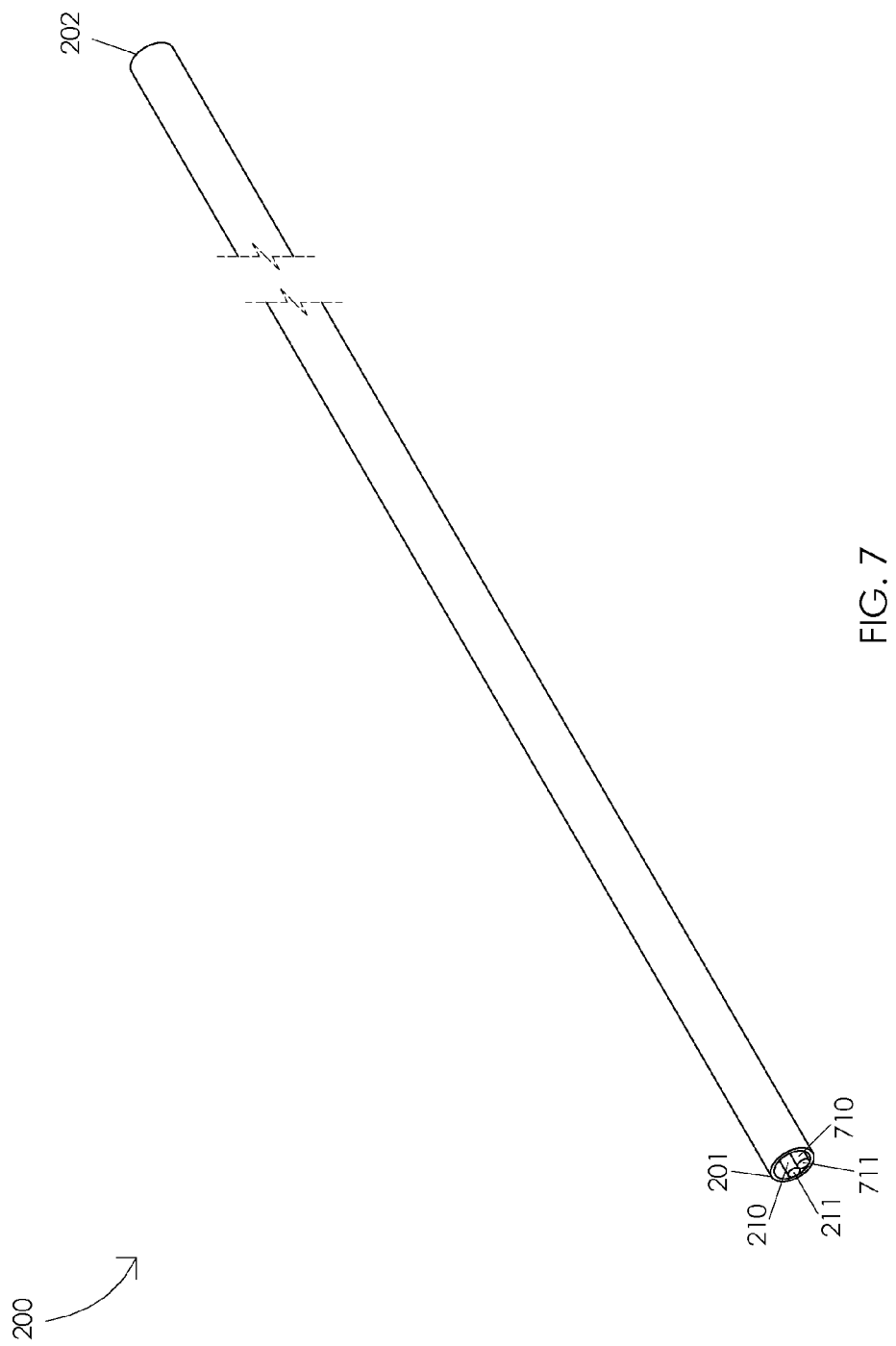
FIG. 7 is a schematic diagram illustrating a flexible housing tube.

FIG. 7 is a schematic diagram illustrating a flexible housing tube 200. Illustratively, an optic fiber 210 may be disposed within flexible housing tube 200. In one or more embodiments, optic fiber 210 may comprise an optic fiber distal end 211 and an optic fiber proximal end 212. Illustratively, optic fiber 210 may be configured to transmit light, e.g., laser light, illumination light, etc. In one or more embodiments, optic fiber 210 may be disposed within flexible housing tube 200 wherein optic fiber distal end 211 may be adjacent to flexible housing tube distal end 201. In one or more embodiments, a portion of optic fiber 210 may be fixed to an inner portion of flexible housing tube 200, e.g., by an adhesive or any suitable fixation means. Illustratively, a cable 710 may be disposed within flexible housing tube 200. In one or more embodiments, cable 710 may comprise a cable distal end 711 and a cable proximal end 712. Illustratively, cable 710 may be disposed within flexible housing tube 200 wherein cable distal end 711 may be adjacent to flexible housing tube distal end 201. Illustratively, a portion of cable 710 may be fixed to a portion of flexible housing tube 200, e.g., by an adhesive or any suitable fixation means. For example, a portion of cable 710 may be fixed to flexible housing tube 200 by a weld, a loop, a tie, etc.

Figure 8:
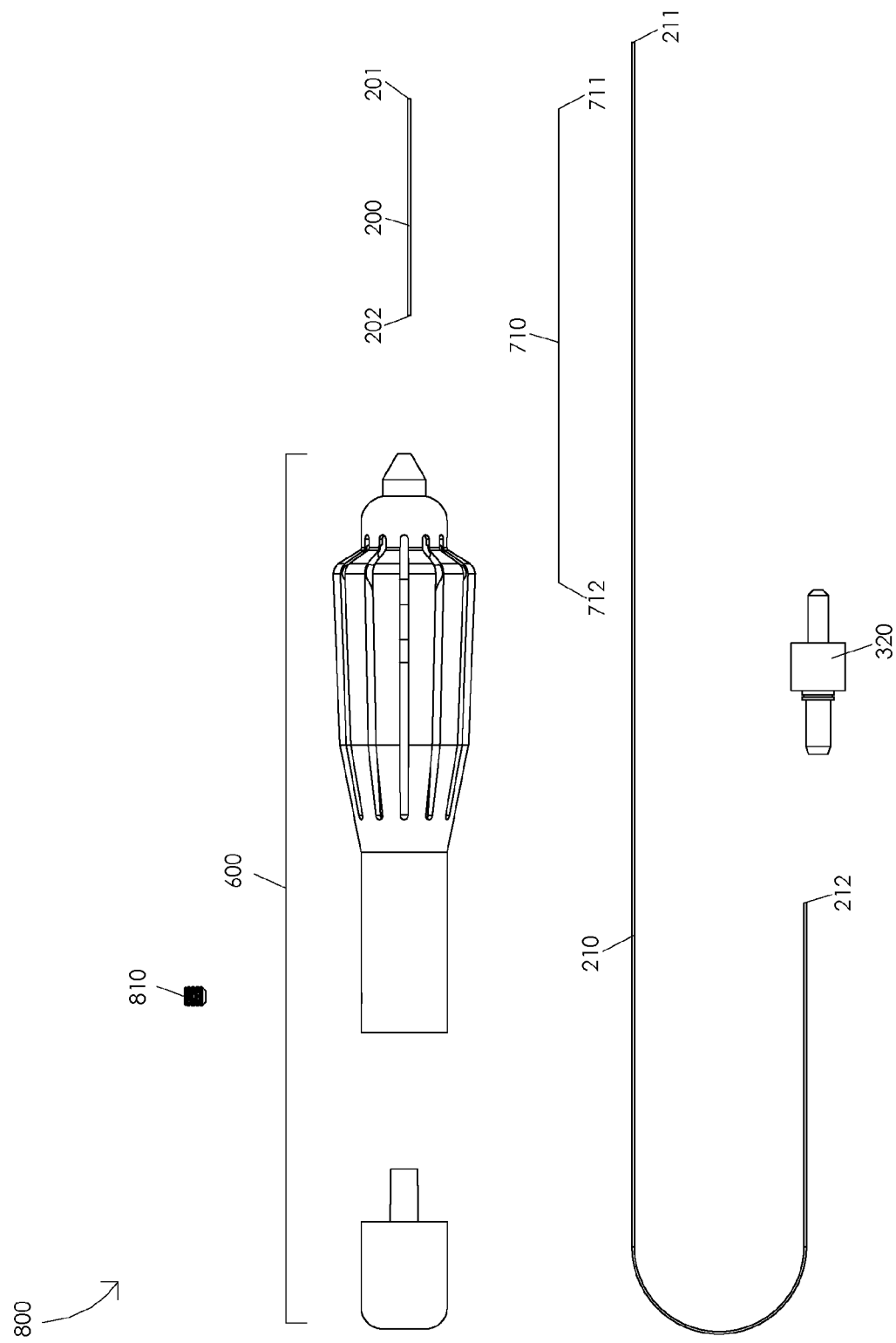
FIG. 8 is a schematic diagram illustrating an exploded view of a steerable laser probe assembly.

FIG. 8 is a schematic diagram illustrating an exploded view of a steerable laser probe assembly 800. In one or more embodiments, a steerable laser probe assembly 800 may comprise a handle 600, a flexible housing tube 200 having a flexible housing tube distal end 201 and a flexible housing tube proximal end 202, an optic fiber 210 having an optic fiber distal end 211 and an optic fiber proximal end 212, a cable 710 having a cable distal end 711 and a cable proximal end 712, a fixation mechanism 810, and a light source interface 320. Illustratively, light source interface 320 may be configured to interface with optic fiber 210, e.g., at optic fiber proximal end 212. In one or more embodiments, light source interface 320 may comprise a standard light source connecter, e.g., an SMA connector.

Illustratively, a portion of flexible housing tube 200 may be fixed to a portion of handle 600, e.g., flexible housing tube proximal end 202 may be fixed to handle distal end 601. In one or more embodiments, a portion of flexible housing tube 200 may be fixed to a portion of handle 600, e.g., by an adhesive or any suitable fixation means. Illustratively, a portion of flexible housing tube 200 may be disposed within flexible housing tube housing 650, e.g., flexible housing tube proximal end 202 may be disposed within flexible housing tube housing 650. In one or more embodiments, a portion of flexible housing tube 200 may be fixed within flexible tube housing 650, e.g., by an adhesive or any suitable fixation means. For example, flexible housing tube 200 may be fixed within flexible housing tube housing 650 by a press fit, a weld, a setscrew, etc.

Illustratively, optic fiber 210 may be disposed within inner bore 640, flexible housing tube housing 650, and flexible housing tube 200. In one or more embodiments, optic fiber 210 may be disposed within flexible housing tube 200 wherein optic fiber distal end 211 may be adjacent to flexible housing tube distal end 201. In one or more embodiments, a portion of optic fiber 210 may be fixed to a portion of flexible housing tube 200, e.g., by an adhesive or any suitable fixation means. Illustratively, cable 710 may be disposed within cable housing 645, inner bore 640, flexible housing tube housing 650, and flexible housing tube 200. In one or more embodiments, cable 710 may be disposed within flexible housing tube 200 wherein cable distal end 711 may be adjacent to flexible housing tube distal end 201. Illustratively, a portion of cable 710 may be fixed to a portion of flexible housing tube 200, e.g., by an adhesive or any suitable fixation means. For example, a portion of cable 710 may be fixed to flexible housing tube 200 by a weld, a loop, a tie, etc. Illustratively, a portion of cable 710 may be fixed within cable housing 645, e.g., by an adhesive or any suitable fixation means. In one or more embodiments, fixation mechanism 810 may be configured to fix a portion of cable 710 within cable housing 645, e.g., fixation mechanism 810 may be disposed within fixation mechanism housing 615 and cable housing 645. Illustratively, fixation mechanism 810 may be configured to fix a portion of cable 710 within cable housing 645, e.g., by a press fit or any suitable fixation means. In one or more embodiments, fixation mechanism 810 may comprise a set screw, e.g., configured to fix a portion of cable within cable housing 645.

Illustratively, a compression of actuation structure 120 may be configured to extend actuation structure distal end 121 relative to actuation structure proximal end 122. In one or more embodiments, an extension of actuation structure distal end 121 relative to actuation structure proximal end 122 may be configured to extend handle distal end 601 relative to handle proximal end 602. Illustratively, an extension of handle distal end 601 relative to handle proximal end 602 may be configured to extend flexible housing tube 200 relative to handle proximal end 602. In one or more embodiments, an extension of flexible housing tube 200 relative to handle proximal end 602 may be configured to extend flexible housing tube 200 relative to cable 710. Illustratively, a portion of cable 710, e.g., a portion of cable 710 fixed to flexible housing tube 200, may be configured to resist an extension of flexible housing tube 200 relative to cable 710. In one or more embodiments, an extension of flexible housing tube 200 relative to cable 710 may be configured to compress a portion of flexible housing tube 200, e.g., a portion of cable 710 fixed to a portion of flexible housing tube 200 may be configured compress a portion of flexible housing tube 200. Illustratively, a compression of a portion of flexible housing tube 200 may be configured to cause flexible housing tube 200 to gradually curve. In one or more embodiments, a gradual curving of flexible housing tube 200 may be configured to gradually curve optic fiber 210. Illustratively, a compression of actuation structure 120 may be configured to gradually curve flexible housing tube 200. In one or more embodiments, a compression of actuation structure 120 may be configured to gradually curve optic fiber 210.

Illustratively, a decompression of actuation structure 120 may be configured to retract actuation structure distal end 121 relative to actuation structure proximal end 122. In one or more embodiments, a retraction of actuation structure distal end 121 relative to actuation structure proximal end 122 may be configured to retract handle distal end 601 relative to handle proximal end 602. Illustratively, a retraction of handle distal end 601 relative to handle proximal end 602 may be configured to retract flexible housing tube 200 relative to handle proximal end 602. In one or more embodiments, a retraction of flexible housing tube 200 relative to handle proximal end 602 may be configured to retract flexible housing tube 200 relative to cable 710. Illustratively, a portion of cable 710, e.g., a portion of cable 710 fixed to flexible housing tube 200, may be configured to facilitate a retraction of flexible housing tube 200 relative to cable 710. In one or more embodiments, a retraction of flexible housing tube 200 relative to cable 710 may be configured to decompress a portion of flexible housing tube 200, e.g., a portion of cable 710 fixed to a portion of flexible housing tube 200 may be configured decompress a portion of flexible housing tube 200. Illustratively, a decompression of a portion of flexible housing tube 200 may be configured to cause flexible housing tube 200 to gradually straighten. In one or more embodiments, a gradual straightening of flexible housing tube 200 may be configured to gradually straighten optic fiber 210. Illustratively, a decompression of actuation structure 120 may be configured to gradually straighten flexible housing tube 200. In one or more embodiments, a decompression of actuation structure 120 may be configured to gradually straighten optic fiber 210.

Figure 9A:
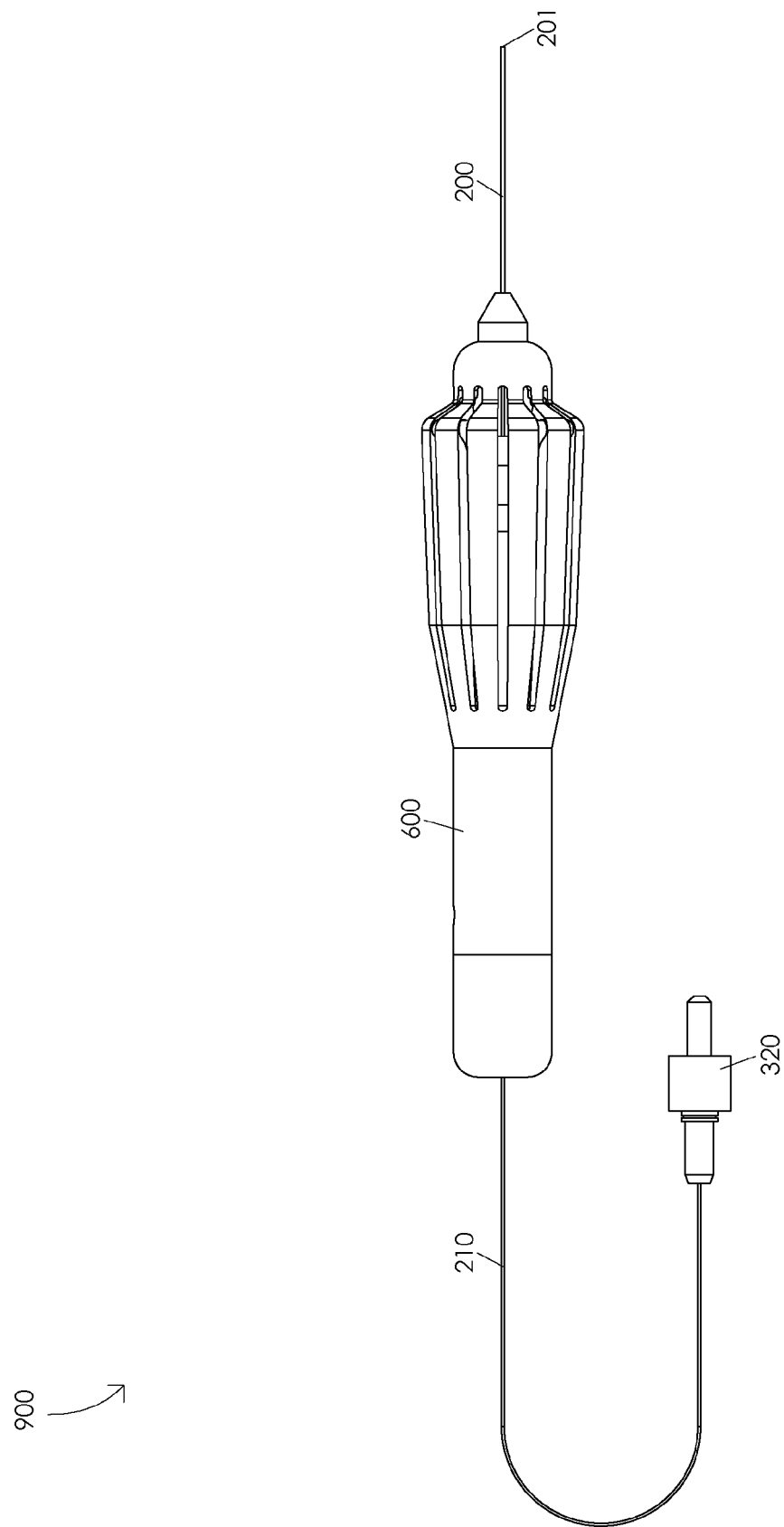
FIGS. 9A, 9B, 9C, 9D, and 9E are schematic diagrams illustrating a gradual curving of an optic fiber.

FIGS. 9A, 9B, 9C, 9D, and 9E are schematic diagrams illustrating a gradual curving of an optic fiber 210. FIG. 9A illustrates a straight optic fiber 900. In one or more embodiments, optic fiber 210 may comprise a straight optic fiber 900, e.g., when actuation structure 120 is fully decompressed. Illustratively, optic fiber 210 may comprise a straight optic fiber 900, e.g., when flexible housing tube 200 is fully retracted relative to cable 710. Illustratively, a line tangent to optic fiber distal end 211 may be parallel to a line tangent to flexible housing tube proximal end 202, e.g., when optic fiber 210 comprises a straight optic fiber 900.

Figure 9B:
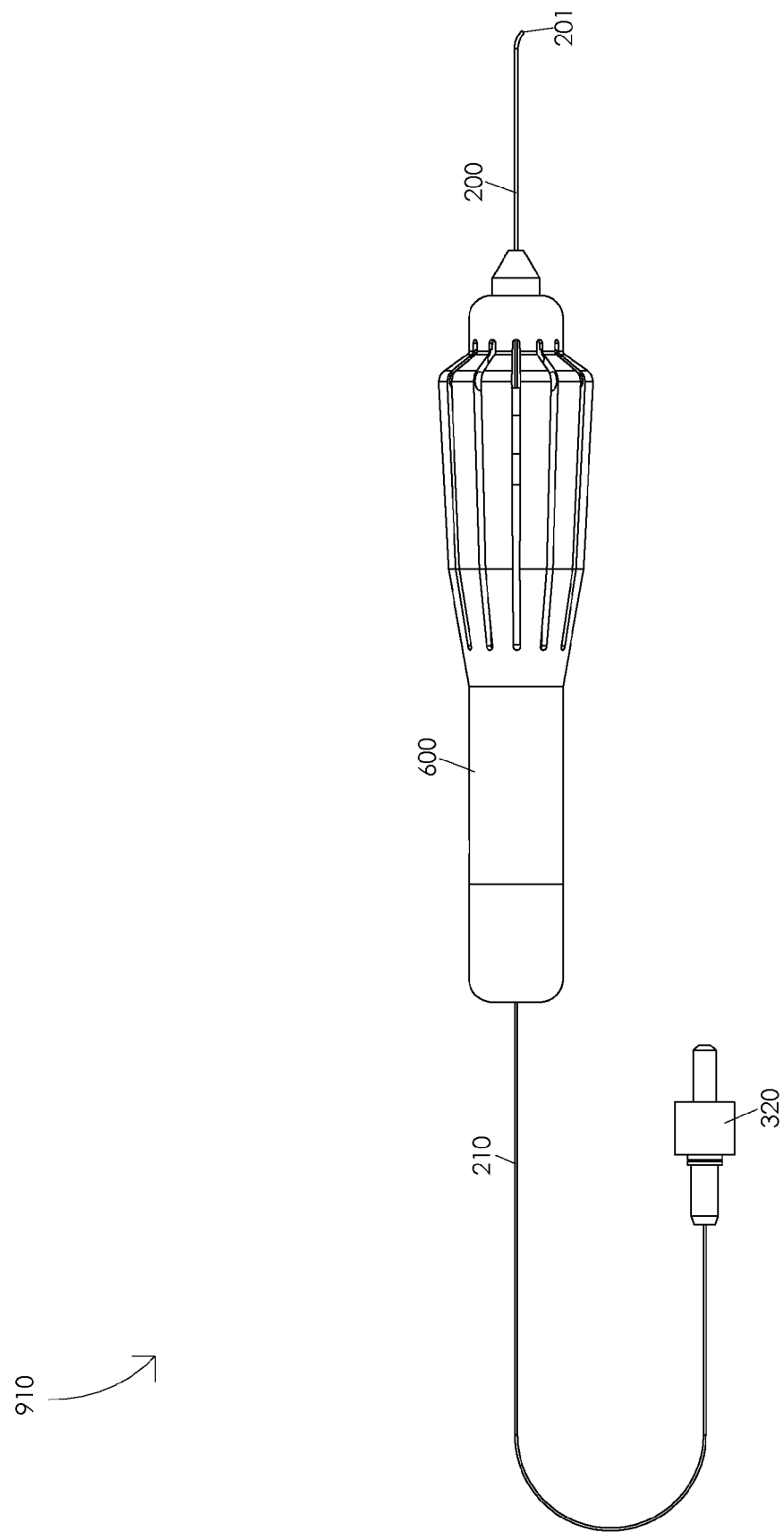

FIG. 9B illustrates an optic fiber in a first curved position 910. In one or more embodiments, a compression of actuation structure 120 may be configured to gradually curve optic fiber 210 from a straight optic fiber 900 to an optic fiber in a first curved position 910. Illustratively, a compression of actuation structure 120 may be configured to extend actuation structure distal end 121 relative to actuation structure proximal end 122. In one or more embodiments, an extension of actuation structure distal 121 end relative to actuation structure proximal end 122 may be configured to extend flexible housing tube 200 relative to cable 710. Illustratively, an extension of flexible housing tube 200 relative to cable 710 may be configured to compress a portion of flexible housing tube 200. In one or more embodiments, a compression of a portion of flexible housing tube 200 may be configured to gradually curve flexible housing tube 200. Illustratively, a gradual curving of flexible housing tube 200 may be configured to gradually curve optic fiber 210, e.g., from a straight optic fiber 900 to an optic fiber in a first curved position 910. In one or more embodiments, a line tangent to optic fiber distal end 211 may intersect a line tangent to flexible housing tube proximal end 202 at a first angle, e.g., when optic fiber 210 comprises an optic fiber in a first curved position 910. In one or more embodiments, the first angle may comprise any angle greater than zero degrees. For example, the first angle may comprise a 45 degree angle.

Figure 9C:
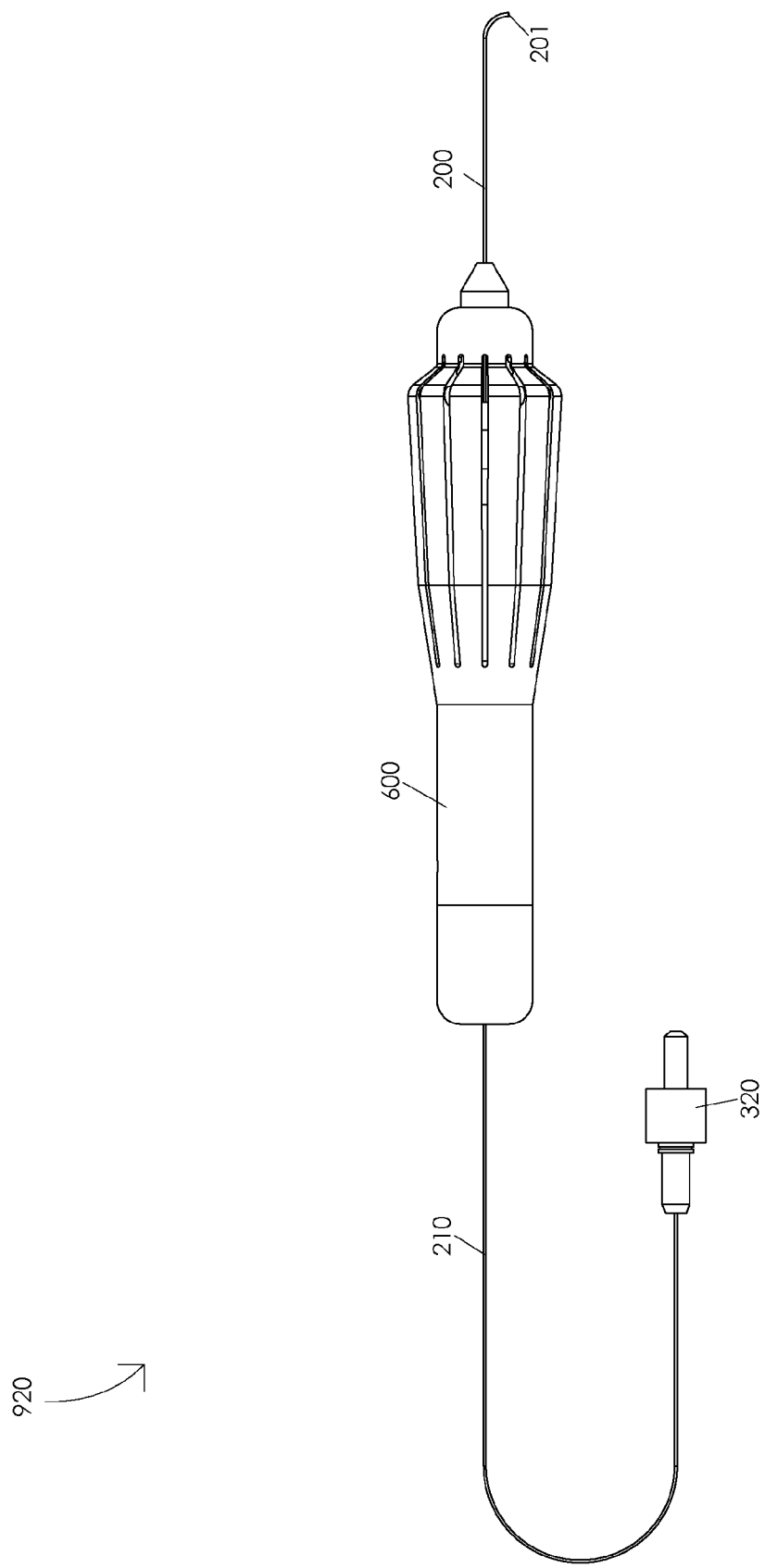

FIG. 9C illustrates an optic fiber in a second curved position 920. In one or more embodiments, a compression of actuation structure 120 may be configured to gradually curve optic fiber 210 from an optic fiber in a first curved position 910 to an optic fiber in a second curved position 920. Illustratively, a compression of actuation structure 120 may be configured to extend actuation structure distal end 121 relative to actuation structure proximal end 122. In one or more embodiments, an extension of actuation structure distal 121 end relative to actuation structure proximal end 122 may be configured to extend flexible housing tube 200 relative to cable 710. Illustratively, an extension of flexible housing tube 200 relative to cable 710 may be configured to compress a portion of flexible housing tube 200. In one or more embodiments, a compression of a portion of flexible housing tube 200 may be configured to gradually curve flexible housing tube 200. Illustratively, a gradual curving of flexible housing tube 200 may be configured to gradually curve optic fiber 210, e.g., from an optic fiber in a first curved position 910 to an optic fiber in a second curved position 920. In one or more embodiments, a line tangent to optic fiber distal end 211 may intersect a line tangent to flexible housing tube proximal end 202 at a second angle, e.g., when optic fiber 210 comprises an optic fiber in a second curved position 920. In one or more embodiments, the second angle may comprise any angle greater than the first angle. For example, the second angle may comprise a 90 degree angle.

Figure 9D:
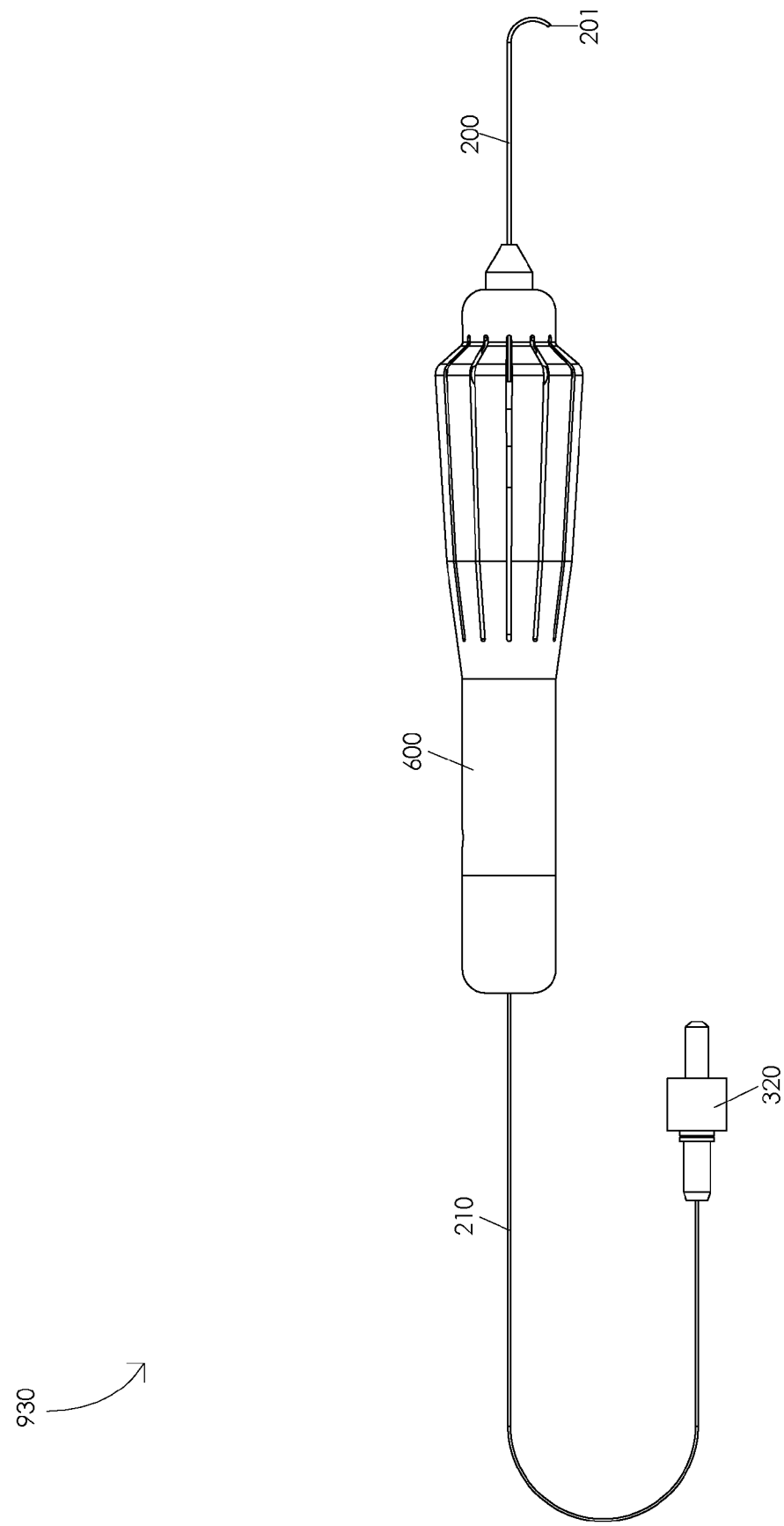

FIG. 9D illustrates an optic fiber in a third curved position 930. In one or more embodiments, a compression of actuation structure 120 may be configured to gradually curve optic fiber 210 from an optic fiber in a second curved position 920 to an optic fiber in a third curved position 930. Illustratively, a compression of actuation structure 120 may be configured to extend actuation structure distal end 121 relative to actuation structure proximal end 122. In one or more embodiments, an extension of actuation structure distal 121 end relative to actuation structure proximal end 122 may be configured to extend flexible housing tube 200 relative to cable 710. Illustratively, an extension of flexible housing tube 200 relative to cable 710 may be configured to compress a portion of flexible housing tube 200. In one or more embodiments, a compression of a portion of flexible housing tube 200 may be configured to gradually curve flexible housing tube 200. Illustratively, a gradual curving of flexible housing tube 200 may be configured to gradually curve optic fiber 210, e.g., from an optic fiber in a second curved position 920 to an optic fiber in a third curved position 930. In one or more embodiments, a line tangent to optic fiber distal end 211 may intersect a line tangent to flexible housing tube proximal end 202 at a third angle, e.g., when optic fiber 210 comprises an optic fiber in a third curved position 930. In one or more embodiments, the third angle may comprise any angle greater than the second angle. For example, the third angle may comprise a 135 degree angle.

Figure 9E:
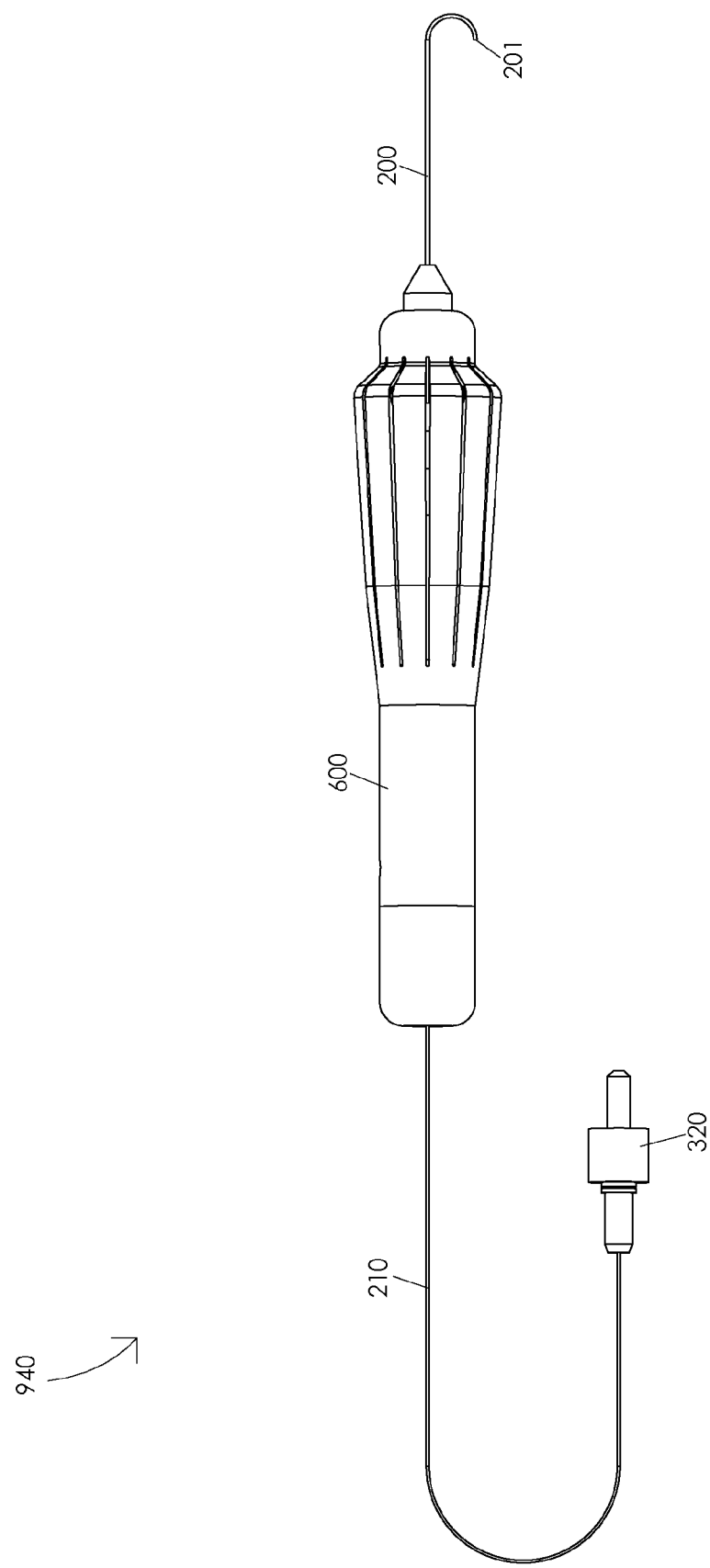

FIG. 9E illustrates an optic fiber in a fourth curved position 940. In one or more embodiments, a compression of actuation structure 120 may be configured to gradually curve optic fiber 210 from an optic fiber in a third curved position 930 to an optic fiber in a fourth curved position 940. Illustratively, a compression of actuation structure 120 may be configured to extend actuation structure distal end 121 relative to actuation structure proximal end 122. In one or more embodiments, an extension of actuation structure distal 121 end relative to actuation structure proximal end 122 may be configured to extend flexible housing tube 200 relative to cable 710. Illustratively, an extension of flexible housing tube 200 relative to cable 710 may be configured to compress a portion of flexible housing tube 200. In one or more embodiments, a compression of a portion of flexible housing tube 200 may be configured to gradually curve flexible housing tube 200. Illustratively, a gradual curving of flexible housing tube 200 may be configured to gradually curve optic fiber 210, e.g., from an optic fiber in a third curved position 930 to an optic fiber in a fourth curved position 940. In one or more embodiments, a line tangent to optic fiber distal end 211 may be parallel to a line tangent to flexible housing tube proximal end 202, e.g., when optic fiber 210 comprises an optic fiber in a fourth curved position 940.

In one or more embodiments, one or more properties of a steerable laser probe may be adjusted to attain one or more desired steerable laser probe features. Illustratively, a length that flexible housing tube distal end 201 extends from handle distal end 601 may be adjusted to vary an amount of compression of actuation structure 120 configured to curve flexible housing tube 200 to a particular curved position. In one or more embodiments, a stiffness of flexible housing tube 200 may be adjusted to vary an amount of compression of actuation structure 120 configured to curve flexible housing tube 200 to a particular curved position. Illustratively, a material comprising flexible housing tube 200 may be adjusted to vary an amount of compression of actuation structure 120 configured to curve flexible housing tube 200 to a particular curved position. In one or more embodiments, a geometry of actuation structure 120 may be adjusted to vary an amount of compression of actuation structure 120 configured to curve flexible housing tube 200 to a particular curved position. Illustratively, one or more locations within flexible housing tube 200 wherein optic fiber 210 may be fixed to a portion of flexible housing tube 200 may be adjusted to vary an amount of compression of actuation structure 120 configured to curve flexible housing tube 200 to a particular curved position.

In one or more embodiments, at least a portion of optic fiber 210 may be enclosed in an optic fiber sleeve configured to, e.g., protect optic fiber 210, vary a stiffness of optic fiber 210, vary an optical property of optic fiber 210, etc. Illustratively, optic fiber 210 may comprise a buffer, a cladding disposed in the buffer, and a core disposed in the cladding. In one or more embodiments, at least a portion of optic fiber 210 may comprise a buffer configured to protect an optical property of optic fiber 210. Illustratively, at least a portion of optic fiber 210 may comprise a buffer configured to protect an optical layer of optic fiber 210, e.g., the buffer may protect an optical layer of a curved portion of optic fiber 210. In one or more embodiments, at least a portion of optic fiber 210 may comprise a polyimide buffer configured to protect an optical property of optic fiber 210. For example, at least a portion of optic fiber 210 may comprise a Kapton buffer configured to protect an optical property of optic fiber 210.

Illustratively, a steerable laser probe may be configured to indicate, e.g., to a surgeon, a direction that optic fiber 210 may curve, e.g., due to a compression of actuation structure 120. In one or more embodiments, a portion of a steerable laser probe, e.g., handle 600, may be marked in a manner configured to indicate a direction that optic fiber 210 may curve. For example, a portion of handle 600 may comprise an arrow marking configured to indicate a direction that optic fiber 210 may curve. Illustratively, a portion of flexible housing tube 200 may comprise a mark configured to indicate a direction that optic fiber 210 may curve. In one or more embodiments, flexible housing tube 200 may comprise a slight curve, e.g., a curve less than 7.5 degrees, when actuation structure 120 is fully decompressed. Illustratively, flexible housing tube 200 may comprise a slight curve, e.g., a curve equal to or greater than 7.5 degrees, when actuation structure 120 is fully decompressed. In one or more embodiments, flexible housing tube 200 may comprise a slight curve configured to indicate a direction that optic fiber 210 may curve, e.g., due to a compression of actuation structure 120.

In one or more embodiments, a location wherein cable 710 may be fixed to flexible housing tube 200 may be adjusted to vary an amount of compression of actuation structure 120 configured to curve flexible housing tube 200 to a particular curved position. For example, a portion of cable 710 may be fixed to an outer portion of flexible housing tube 200. Illustratively, cable 710 may be fixed to flexible housing tube 200 at a plurality of fixation points, e.g., to vary one or more properties of a steerable laser probe. In one or more embodiments, a length of cable 710 may be adjusted to vary an amount of compression of actuation structure 120 configured to curve flexible housing tube 200 to a particular curved position. Illustratively, a steerable laser probe may comprise one or more redundant cables 710. In one or more embodiments, one or more redundant cables 710 may be configured to maintain a particular curved position of flexible housing tube 200, e.g., in the event that cable 710 breaks or fails. Illustratively, one or more redundant cables 710 may be configured to maintain a particular curved position of flexible housing tube 200, e.g., in the event that a cable 710 fixation means fails. In one or more embodiments, one or more redundant cables 710 may be configured to maintain a particular curved position of flexible housing tube 200, e.g., in the event that cable 710 is no longer configured to maintain the particular curved position of flexible housing tube 200. Illustratively, one or more redundant cables 710 may be configured to maintain a particular curved position of flexible housing tube 200 wherein cable 710 is also configured to maintain the particular curved position of flexible housing tube 200.

In one or more embodiments, flexible housing tube 200 may comprise an access window configured to allow access to a portion cable 710. Illustratively, cable 710 may be fixed to a portion of flexible housing tube 200, e.g., by looping a portion of cable 710 through an aperture in flexible housing tube 200. In one or more embodiments, cable 710 may be fixed to a portion of flexible housing tube 200, e.g., by a purely mechanical means. For example, cable 710 may be fixed to a portion of flexible housing tube 200 in a manner other than by an adhesive, a weld, etc. Illustratively, cable 710 may be fixed to a portion of flexible housing tube 200 wherein a portion of cable 710 is configured to fail at a first applied failure force and a fixation means that fixes a portion of cable 710 to a portion of flexible housing tube 200 is configured to fail at a second applied failure force. In one or more embodiments, the second applied failure force may be greater than the first applied failure force.

Figure 10A:
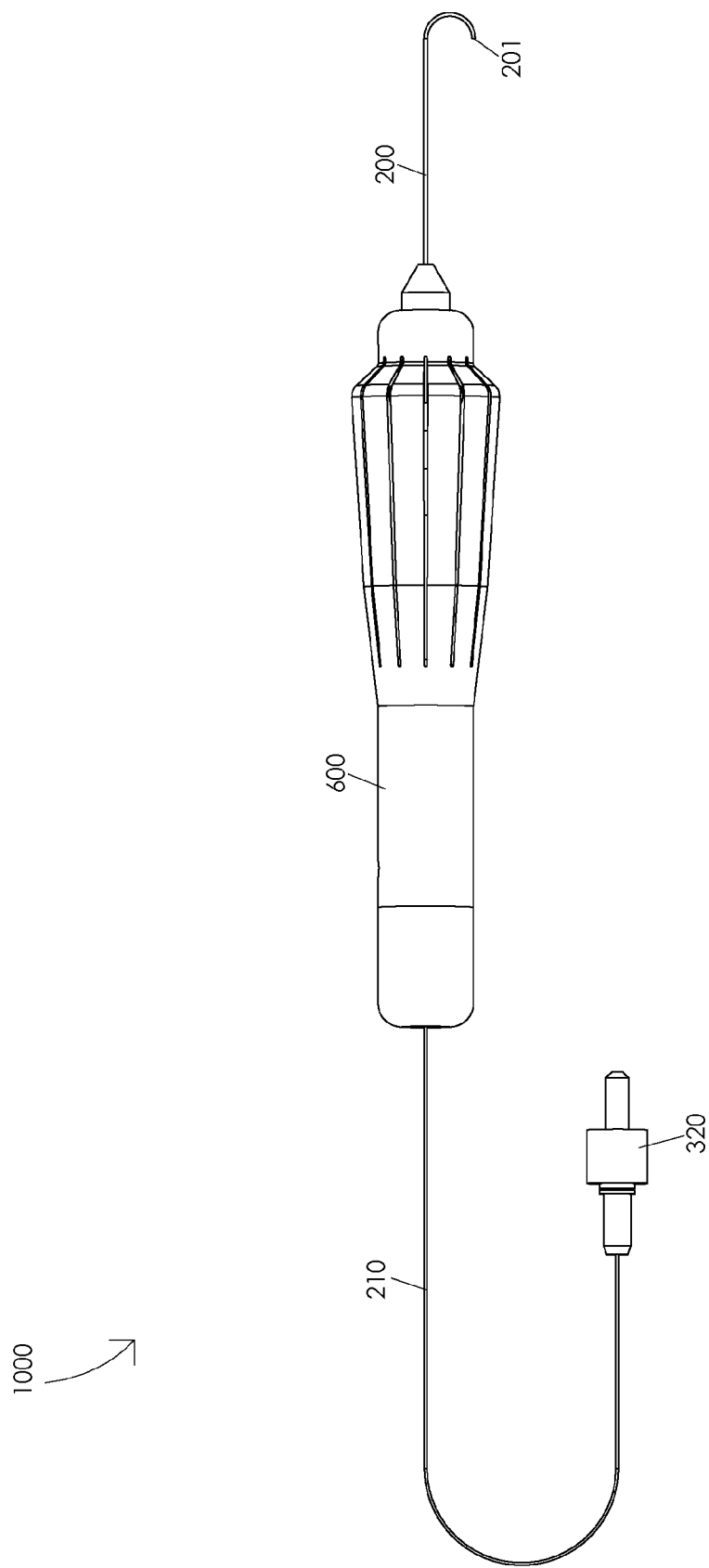
FIGS. 10A, 10B, 10C, 10D, and 10E are schematic diagrams illustrating a gradual straightening of an optic fiber.

FIGS. 10A, 10B, 10C, 10D, and 10E are schematic diagrams illustrating a gradual straightening of an optic fiber 210. FIG. 10A illustrates a fully curved optic fiber 1000. In one or more embodiments, optic fiber 210 may comprise a fully curved optic fiber 1000, e.g., when actuation structure 120 is fully compressed. Illustratively, optic fiber 210 may comprise a fully curved optic fiber 1000, e.g., when flexible housing tube 200 is fully extended relative to wire 710. In one or more embodiments, a line tangent to optic fiber distal end 211 may be parallel to a line tangent to flexible housing tube proximal end 202, e.g., when optic fiber 210 comprises a fully curved optic fiber 1000.

Figure 10B:
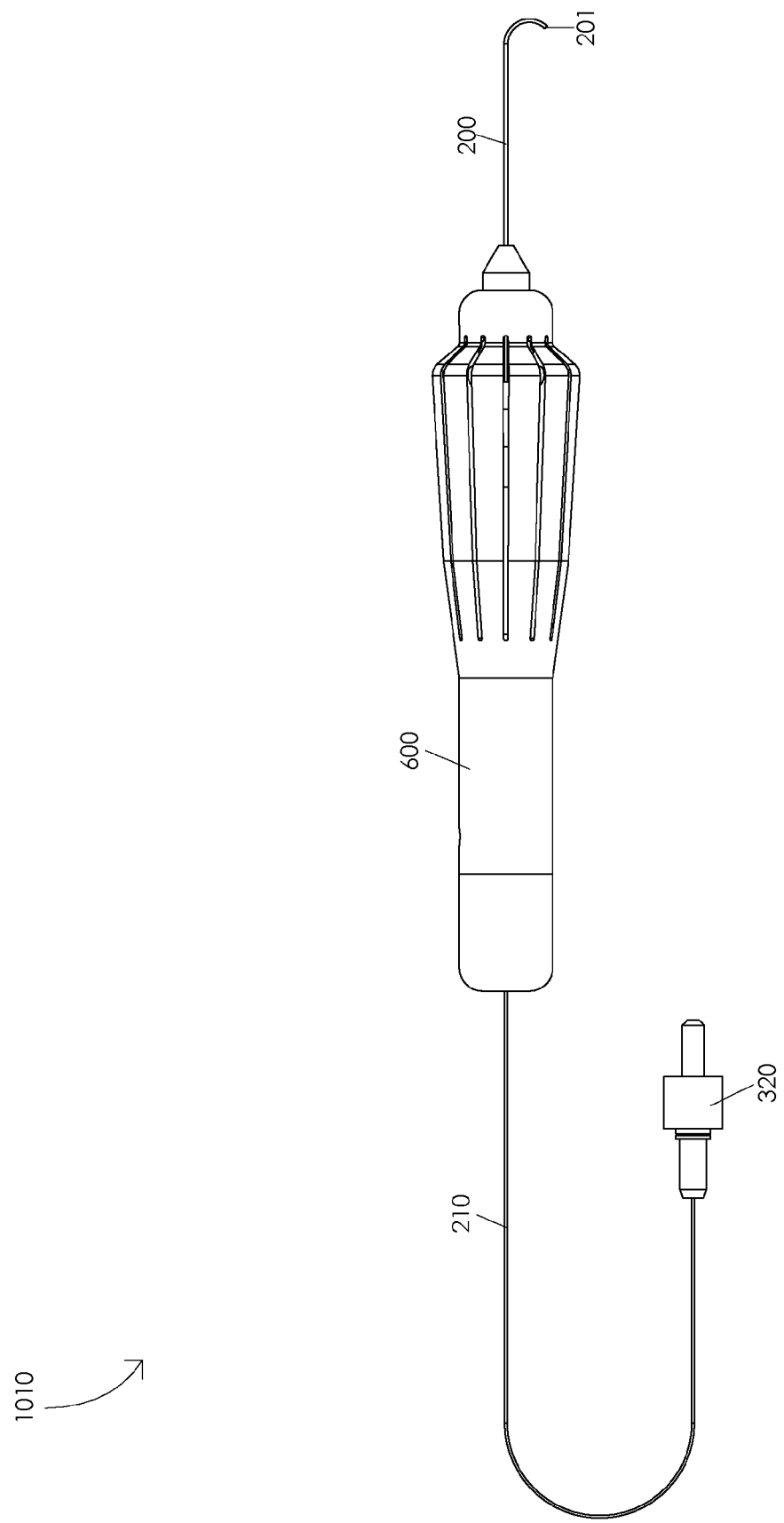

FIG. 10B illustrates an optic fiber in a first partially straightened position 1010. In one or more embodiments, a decompression of actuation structure 120 may be configured to gradually straighten optic fiber 210 from a fully curved optic fiber 1000 to an optic fiber in a first partially straightened position 1010. Illustratively, a decompression of actuation structure 120 may be configured to retract actuation structure distal end 121 relative to actuation structure proximal end 122. In one or more embodiments, a retraction of actuation structure distal end 121 relative to actuation structure proximal end 122 may be configured to retract flexible housing tube 200 relative to cable 710. Illustratively, a portion of cable 710, e.g., a portion of cable 710 fixed to a portion of flexible housing tube 200, may be configured to facilitate a retraction of flexible housing tube 200 relative to cable 710. In one or more embodiments, a retraction of flexible housing tube 200 relative to cable 710 may be configured to decompress a portion of flexible housing tube 200. Illustratively, a decompression of a portion of flexible housing tube 200 may be configured to gradually straighten flexible housing tube 200. In one or more embodiments, a gradual straightening of flexible housing tube 200 may be configured to gradually straighten optic fiber 210, e.g., from a fully curved optic fiber 1000 to an optic fiber in a first partially straightened position 1010. Illustratively, a line tangent to optic fiber distal end 211 may intersect a line tangent to flexible housing tube proximal end 202 at a first partially straightened angle, e.g., when optic fiber 210 comprises an optic fiber in a first partially straightened position 1010. In one or more embodiments, the first partially straightened angle may comprise any angle less than 180 degrees. For example, the first partially straightened angle may comprise a 135 degree angle.

Figure 10C:
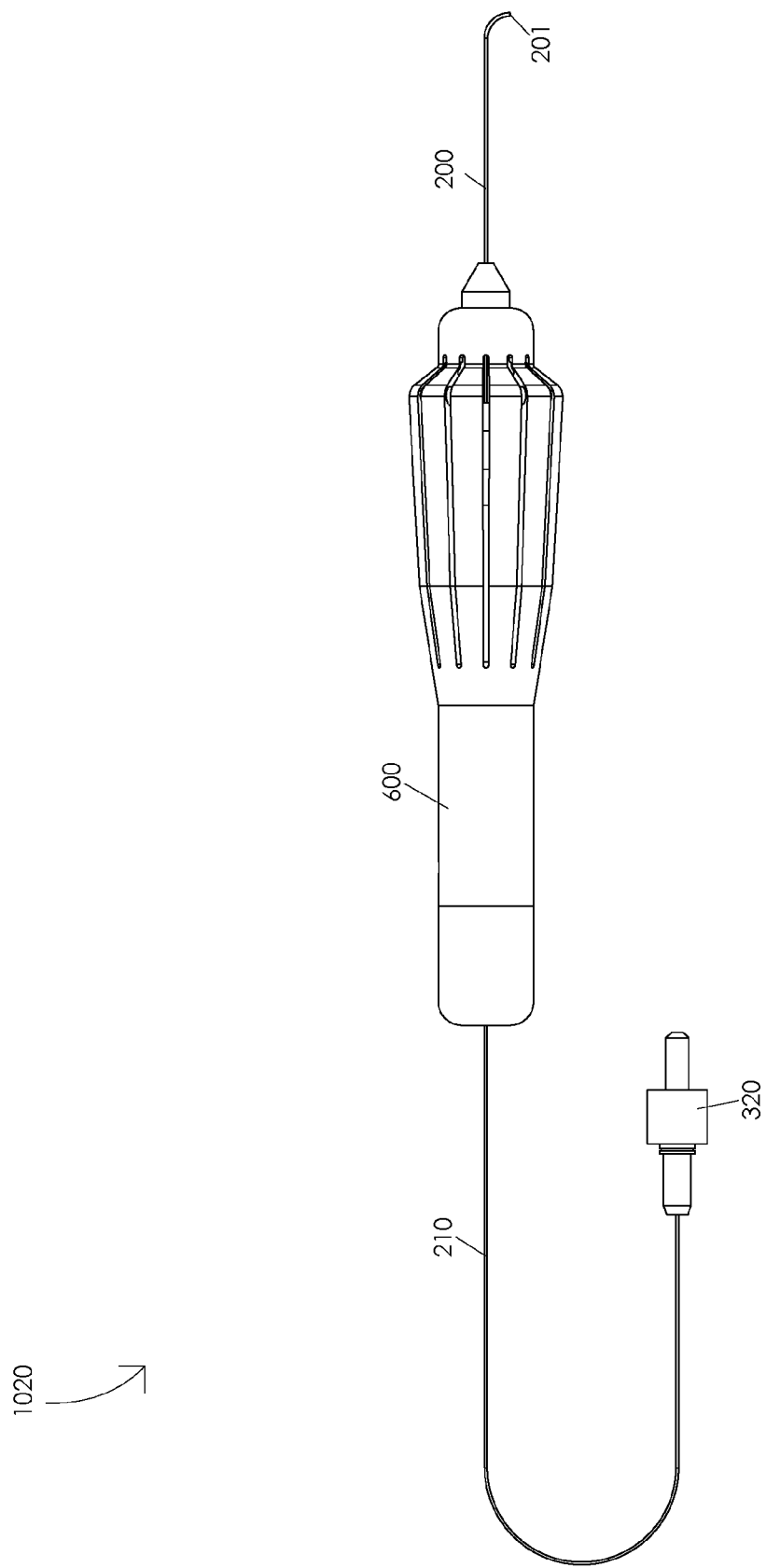

FIG. 10C illustrates an optic fiber in a second partially straightened position 1020. In one or more embodiments, a decompression of actuation structure 120 may be configured to gradually straighten optic fiber 210 from an optic fiber in a first partially straightened position 1010 to an optic fiber in a second partially straightened position 1020. Illustratively, a decompression of actuation structure 120 may be configured to retract actuation structure distal end 121 relative to actuation structure proximal end 122. In one or more embodiments, a retraction of actuation structure distal end 121 relative to actuation structure proximal end 122 may be configured to retract flexible housing tube 200 relative to cable 710. Illustratively, a portion of cable 710, e.g., a portion of cable 710 fixed to a portion of flexible housing tube 200, may be configured to facilitate a retraction of flexible housing tube 200 relative to cable 710. In one or more embodiments, a retraction of flexible housing tube 200 relative to cable 710 may be configured to decompress a portion of flexible housing tube 200. Illustratively, a decompression of a portion of flexible housing tube 200 may be configured to gradually straighten flexible housing tube 200. In one or more embodiments, a gradual straightening of flexible housing tube 200 may be configured to gradually straighten optic fiber 210, e.g., from an optic fiber in a first partially straightened position 1010 to an optic fiber in a second partially straightened position 1020. Illustratively, a line tangent to optic fiber distal end 211 may intersect a line tangent to flexible housing tube proximal end 202 at a second partially straightened angle, e.g., when optic fiber 210 comprises an optic fiber in a second partially straightened position 1020. In one or more embodiments, the second partially straightened angle may comprise any angle less than the first partially straightened angle. For example, the second partially straightened angle may comprise a 90 degree angle.

Figure 10D:
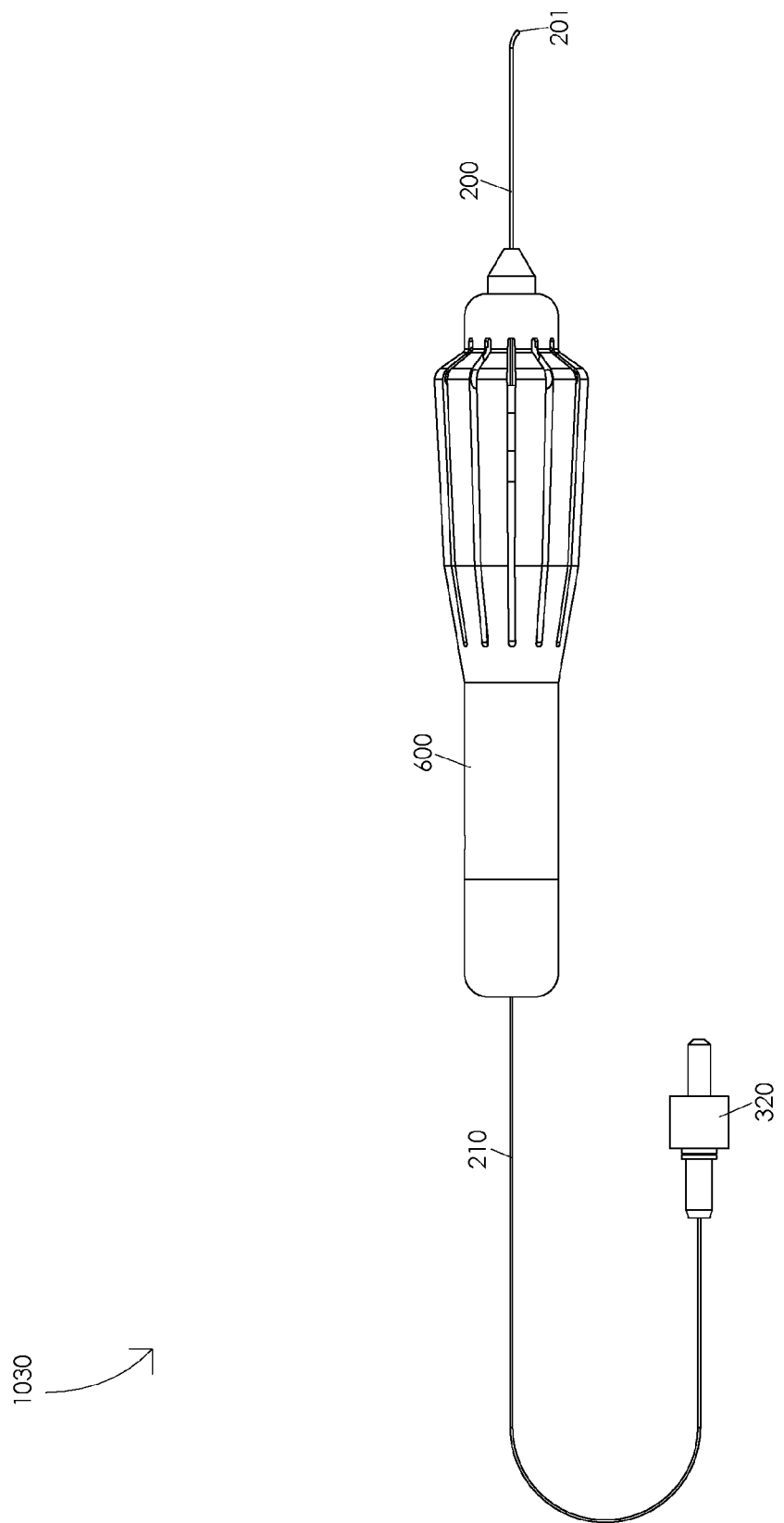

FIG. 10D illustrates an optic fiber in a third partially straightened position 1030. In one or more embodiments, a decompression of actuation structure 120 may be configured to gradually straighten optic fiber 210 from an optic fiber in a second partially straightened position 1020 to an optic fiber in a third partially straightened position 1030. Illustratively, a decompression of actuation structure 120 may be configured to retract actuation structure distal end 121 relative to actuation structure proximal end 122. In one or more embodiments, a retraction of actuation structure distal end 121 relative to actuation structure proximal end 122 may be configured to retract flexible housing tube 200 relative to cable 710. Illustratively, a portion of cable 710, e.g., a portion of cable 710 fixed to a portion of flexible housing tube 200, may be configured to facilitate a retraction of flexible housing tube 200 relative to cable 710. In one or more embodiments, a retraction of flexible housing tube 200 relative to cable 710 may be configured to decompress a portion of flexible housing tube 200. Illustratively, a decompression of a portion of flexible housing tube 200 may be configured to gradually straighten flexible housing tube 200. In one or more embodiments, a gradual straightening of flexible housing tube 200 may be configured to gradually straighten optic fiber 210, e.g., from an optic fiber in a second partially straightened position 1020 to an optic fiber in a third partially straightened position 1030. Illustratively, a line tangent to optic fiber distal end 211 may intersect a line tangent to flexible housing tube proximal end 202 at a third partially straightened angle, e.g., when optic fiber 210 comprises an optic fiber in a third partially is straightened position 1030. In one or more embodiments, the third partially straightened angle may comprise any angle less than the second partially straightened angle. For example, the third partially straightened angle may comprise a 45 degree angle.

Figure 10E:
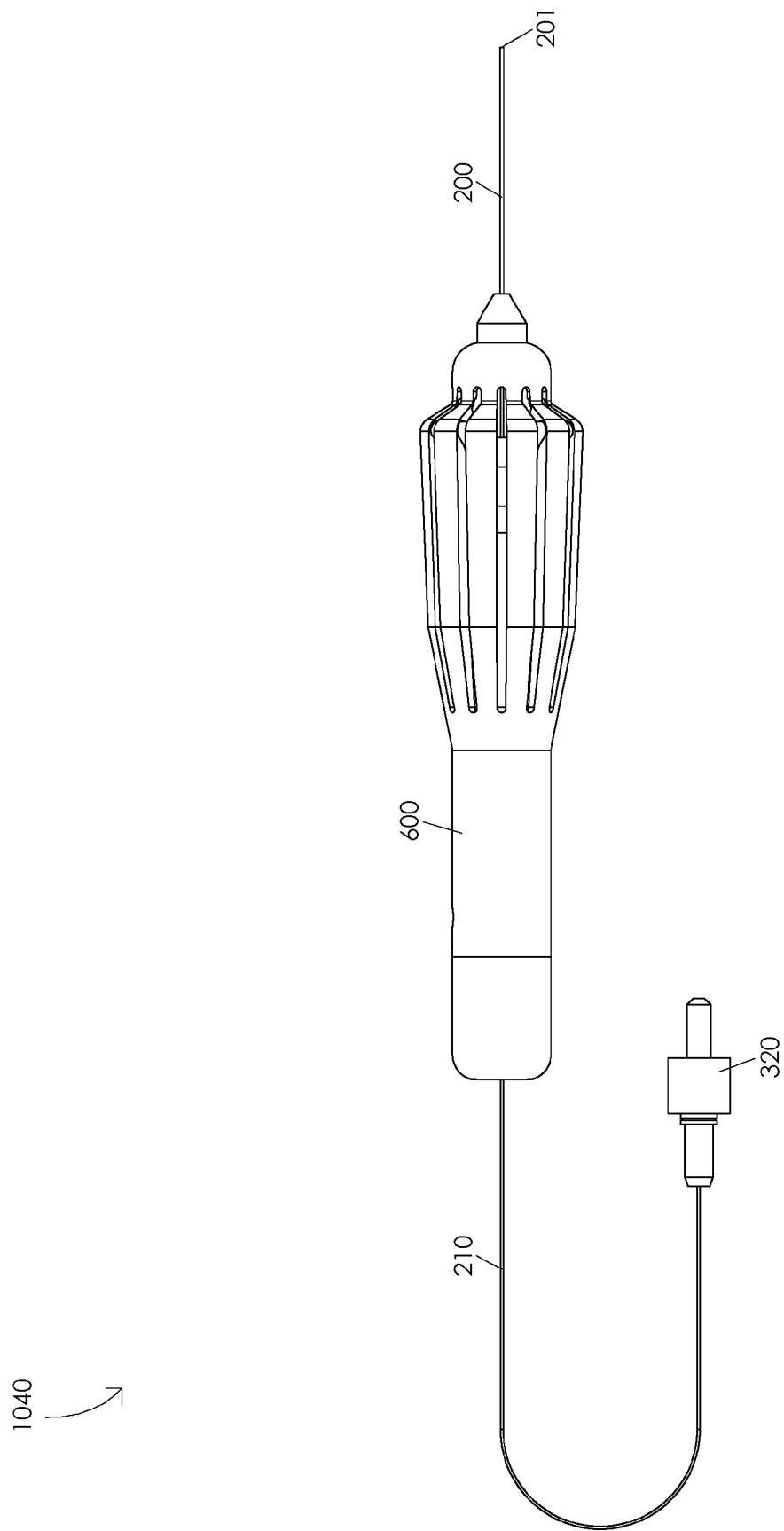

FIG. 10E illustrates an optic fiber in a fully straightened position 1040. In one or more embodiments, a decompression of actuation structure 120 may be configured to gradually straighten optic fiber 210 from an optic fiber in a third partially straightened position 1030 to an optic fiber in a fully straightened position 1040. Illustratively, a decompression of actuation structure 120 may be configured to retract actuation structure distal end 121 relative to actuation structure proximal end 122. In one or more embodiments, a refraction of actuation structure distal end 121 relative to actuation structure proximal end 122 may be configured to retract flexible housing tube 200 relative to cable 710. Illustratively, a portion of cable 710, e.g., a portion of cable 710 fixed to a portion of flexible housing tube 200, may be configured to facilitate a retraction of flexible housing tube 200 relative to cable 710. In one or more embodiments, a retraction of flexible housing tube 200 relative to cable 710 may be configured to decompress a portion of flexible housing tube 200. Illustratively, a decompression of a portion of flexible housing tube 200 may be configured to gradually straighten flexible housing tube 200. In one or more embodiments, a gradual straightening of flexible housing tube 200 may be configured to gradually straighten optic fiber 210, e.g., from an optic fiber in a third partially straightened position 1030 to an optic fiber in a fully straightened position 1040. Illustratively, a line tangent to optic fiber distal end 211 may be parallel to a line tangent to flexible housing tube proximal end 202, e.g., when optic fiber 210 comprises an optic fiber in a fully straightened position 1040.

Illustratively, a surgeon may aim optic fiber distal end 211 at any of a plurality of targets within an eye, e.g., to perform a photocoagulation procedure, to illuminate a surgical target site, etc. In one or more embodiments, a surgeon may aim optic fiber distal end 211 at any target within a particular transverse plane of the inner eye by, e.g., rotating handle 600 to orient flexible housing tube 200 in an orientation configured to cause a curvature of flexible housing tube 200 within the particular transverse plane of the inner eye and varying an amount of compression of actuation structure 120. Illustratively, a surgeon may aim optic fiber distal end 211 at any target within a particular sagittal plane of the inner eye by, e.g., rotating handle 600 to orient flexible housing tube 200 in an orientation configured to cause a curvature of flexible housing tube 200 within the particular sagittal plane of the inner eye and varying an amount of compression of actuation structure 120. In one or more embodiments, a surgeon may aim optic fiber distal end 211 at any target within a particular frontal plane of the inner eye by, e.g., varying an amount of compression of actuation structure 120 to orient a line tangent to optic fiber distal end 211 wherein the line tangent to optic fiber distal end 211 is within the particular frontal plane of the inner eye and rotating handle 600. Illustratively, a surgeon may aim optic fiber distal end 211 at any target located outside of the particular transverse plane, the particular sagittal plane, and the particular frontal plane of the inner eye, e.g., by varying a rotational orientation of handle 600 and varying an amount of compression of actuation structure 120. In one or more embodiments, a surgeon may aim optic fiber distal end 211 at any target of a plurality of targets within an eye, e.g., without increasing a length of a portion of a steerable laser probe within the eye. Illustratively, a surgeon may aim optic fiber distal end 211 at any target of a plurality of targets within an eye, e.g., without decreasing a length of a portion of a steerable laser probe within the eye.

The foregoing description has been directed to particular embodiments of this invention. It will be apparent; however, that other variations and modifications may be made to the described embodiments, with the attainment of some or all of their advantages. Specifically, it should be noted that the principles of the present invention may be implemented in any system. Furthermore, while this description has been written in terms of a medical device, the teachings of the present invention are equally suitable to any systems where the functionality may be employed. Therefore, it is the object of the appended claims to cover all such variations and modifications as come within the true spirit and scope of the invention.

What is claimed is:

1. An instrument comprising:
   a handle having a handle distal end and a handle proximal end;
   an actuation structure of the handle having an actuation structure distal end and an actuation structure proximal end, the actuation structure having a mass in a range of 0.01 to 0.03 pounds;
   a fixation mechanism housing of the handle;
   a handle end plug wherein a portion of the handle end plug is disposed in an inner bore of the handle wherein the portion of the handle end plug is adjacent to the fixation mechanism housing;
   a cable housing of the handle end plug;
   a plurality of actuation arms of the actuation structure;

an expansion joint of each actuation arm of the plurality of actuation arms wherein an expansion of a particular expansion joint of a particular actuation arm is configured to expand the expansion joint of each actuation arm of the plurality of actuation arms;

a single flexible housing tube having a flexible housing tube distal end and a flexible housing tube proximal end, the flexible housing tube proximal end disposed in a flexible housing tube housing wherein the flexible housing tube is fixed in the flexible housing tube housing and wherein the flexible housing tube has dimensions configured for performing ophthalmic surgical procedures and wherein the flexible housing tube is configured to reduce friction as the flexible housing tube is inserted into a cannula and removed from the cannula, the flexible housing tube having an ultimate tensile strength in a range of 1000 to 1100 MPa;

an optic fiber having an optic fiber distal end and an optic fiber proximal end, the optic fiber disposed within the inner bore of the handle, the flexible housing tube housing, and the flexible housing tube wherein the optic fiber distal end is adjacent to the flexible housing tube distal end and wherein the optic fiber is fixed to a portion of the flexible housing tube, the optic fiber configured to transmit laser light;

a cable having a cable distal end and a cable proximal end, the cable disposed in the cable housing, the inner bore, and the flexible housing tube wherein the cable distal end is adjacent to the flexible housing tube distal end and the optic fiber distal end and wherein the cable is fixed to the flexible housing tube by a weld and wherein the cable is configured to fail at a first applied failure force and wherein the weld is configured to fail at a second applied failure force and wherein the second applied failure force is greater than the first applied failure force; and a fixation mechanism disposed in the fixation mechanism housing wherein the fixation mechanism fixes a portion of the cable in the cable housing and wherein the cable is configured to resist an extension of the flexible housing tube relative to the cable.

2. The instrument of claim 1 wherein the mass of the actuation structure is 0.024 pounds.

3. The instrument of claim 1 wherein the actuation structure has a density in a range of 0.02 to 0.06 pounds per cubic inch.

4. The instrument of claim 3 wherein the actuation structure has a volume in a range of 0.3 to 0.7 cubic inches.

5. The instrument of claim 3 wherein the density of the actuation structure is 0.041 pounds per cubic inch.

6. The instrument of claim 4 wherein the volume of the actuation structure is 0.577 cubic inches.

7. The instrument of claim 1 wherein a compression of the actuation structure is configured to gradually curve the optic fiber.

8. The instrument of claim 7 wherein the compression of the actuation structure is configured to extend the actuation structure distal end relative to the actuation structure proximal end in a range of 0.02 to 0.06 inches.

9. The instrument of claim 1 wherein a decompression of the actuation structure is configured to gradually straighten the optic fiber.

10. The instrument of claim 9 wherein the decompression of the actuation structure is configured to retract the actuation structure distal end relative to the actuation structure proximal end in a range of 0.02 to 0.06 inches.

11. The instrument of claim 1 wherein an application of a force having a magnitude in a range of 0.6 to 1.6 pounds to a portion of the actuation structure is configured to curve the optic fiber at least 45 degrees.

12. The instrument of claim 11 wherein the application of the force having the magnitude in the range of 0.6 to 1.6 pounds to the portion of the actuation structure is configured to curve the optic fiber at least 90 degrees.

13. The instrument of claim 12 wherein the application of the force having the magnitude in the range of 0.6 to 1.6 pounds to the portion of the actuation structure is configured to curve the optic fiber at least 135 degrees.

14. The instrument of claim 13 wherein the application of the force having the magnitude in the range of 0.6 to 1.6 pounds to the portion of the actuation structure is configured to curve the optic fiber 180 degrees.

15. The instrument of claim 1 wherein the fixation mechanism is a setscrew.

16. The instrument of claim 1 wherein the flexible housing tube is manufactured from nitinol.

17. The instrument of claim 1 wherein a compression of the actuation structure is configured to curve the optic fiber within an eye.

18. The instrument of claim 17 wherein the compression of the actuation structure is configured to curve the optic fiber within the eye without increasing an amount of the instrument within the eye.

19. The instrument of claim 17 wherein the compression of the actuation structure is configured to curve the optic fiber within the eye without decreasing an amount of the instrument within the eye.

20. The instrument of claim 1 further comprising:
an access window of the flexible housing tube.

* * * * *